US010736880B2

(12) United States Patent
Refuerzo et al.

(10) Patent No.: US 10,736,880 B2
(45) Date of Patent: Aug. 11, 2020

(54) THERAPEUTICS FOR PRETERM LABOR MANAGEMENT

(71) Applicants: THE BOARD OF REGENTS OF THE UNIVERSITY OF TEXAS SYSTEM, Austin, TX (US); THE METHODIST HOSPITAL, Houston, TX (US)

(72) Inventors: Jerrie S. Refuerzo, Houston, TX (US); Biana Godin, Houston, TX (US); Monica Longo, Houston, TX (US)

(73) Assignees: THE BOARD OF REGENTS OF THE UNIVERSITY OF TEXAS SYSTEMS, Austin, TX (US); THE METHODIST HOSPITAL, Houston, TX (US)

( * ) Notice: Subject to any disclaimer, the term of this patent is extended or adjusted under 35 U.S.C. 154(b) by 0 days.

(21) Appl. No.: 16/063,312

(22) PCT Filed: Dec. 19, 2016

(86) PCT No.: PCT/US2016/067449
§ 371 (c)(1),
(2) Date: Jun. 18, 2018

(87) PCT Pub. No.: WO2017/106814
PCT Pub. Date: Jun. 22, 2017

(65) Prior Publication Data
US 2018/0360806 A1 Dec. 20, 2018

Related U.S. Application Data

(60) Provisional application No. 62/269,651, filed on Dec. 18, 2015.

(51) Int. Cl.
| | |
|---|---|
| *A61K 31/405* | (2006.01) |
| *A61K 38/095* | (2019.01) |
| *A61K 47/69* | (2017.01) |
| *A61K 9/00* | (2006.01) |
| *A61K 9/127* | (2006.01) |
| *A61K 47/62* | (2017.01) |
| *C07K 7/16* | (2006.01) |
| *A61P 15/06* | (2006.01) |
| *A61P 15/00* | (2006.01) |

(52) U.S. Cl.
CPC .......... *A61K 31/405* (2013.01); *A61K 9/0019* (2013.01); *A61K 9/127* (2013.01); *A61K 9/1271* (2013.01); *A61K 38/095* (2019.01); *A61K 47/62* (2017.08); *A61K 47/6911* (2017.08); *A61P 15/00* (2018.01); *A61P 15/06* (2018.01); *C07K 7/16* (2013.01)

(58) Field of Classification Search
CPC .. A61K 31/405; A61K 47/62; A61K 47/6911; A61K 9/0019; A61K 9/127; A61K 9/1271; A61K 38/095; A61P 15/00; A61P 15/06; C07K 7/16
See application file for complete search history.

(56) References Cited

U.S. PATENT DOCUMENTS

| | | |
|---|---|---|
| 5,541,101 A | 7/1996 | Saji et al. |
| 9,101,569 B2 | 8/2015 | Rohner-Jeanrenaud et al. |
| 2003/0027815 A1 | 2/2003 | Failli et al. |
| 2006/0165744 A1 | 7/2006 | Jamil et al. |
| 2007/0032410 A1 | 2/2007 | Quay et al. |
| 2010/0260675 A1 | 10/2010 | Huang et al. |
| 2012/0270785 A1 | 10/2012 | McGregor et al. |

FOREIGN PATENT DOCUMENTS

| | | | |
|---|---|---|---|
| EP | 0249561 | 12/1987 | |
| EP | 2460868 | 6/2012 | |
| WO | WO 1995/022345 | 8/1995 | |
| WO | WO 2004/034981 | 4/2004 | |
| WO | WO 2004/062563 | 7/2004 | |
| WO | WO 2005/000266 | 1/2005 | |
| WO | WO 2005/053705 | 6/2005 | |
| WO | WO2013075176 | * 11/2012 | ............. A61K 31/18 |
| WO | WO 2014/186843 | 11/2014 | |
| WO | WO 2015/075032 | 5/2015 | |

OTHER PUBLICATIONS

Wang et al. Application of poly(ethylene glycol)-distearoylphosphatidylethanolamine (PEG-DSPE_ block copolymers and their derivatives as nanomaterials in drug delivery. Int Journal of Nanomedicine, 2012, vol. 7, pp. 4185-4198. (Year: 2012).*
Abou-Ghannam et al. Indomethacin in Pregnancy: Applications and Safety. Am J Perinatol 2012. vol. 29, pp. 175-186. (Year: 2012).*
Smith et al. Nifedipine in pregnancy. BJOG, 2005, pp. 1-35. (Year: 2005).*
Paul et al. Preventing preterm birth: New approaches to labour therapeutics using Nanoparticles. Best Practice & Research Clinical Obstetrics and Gynaecology, vol. 52, pp. 48-59. (Year: 2018).*
Bajoria, et al. "Liposomal thyroxine: a noninvasive model for transplacental fetal therapy." *The Journal of Clinical Endocrinology & Metabolism* 82.10 (1997): 3271-3277.
Böttcher, B., et al. "A first-in-human study of PDC31 (prostaglandin F2α receptor inhibitor) in primary dysmenorrhea." *Human Reproduction* 29.11 (2014): 2465-2473.
Extended European Search Report Issued in European Application No. 16876890.1, dated Jul. 9, 2019.
Hicks, C., et al. "The Nonpeptide Oxytocin Receptor Agonist WAY 267,464: Receptor-Binding Profile, Prosocial Effects and Distribution of c-Fos Expression in Adolescent Rats." *Journal of Neuroendocrinology* 24.7 (2012): 1012-1029.

(Continued)

*Primary Examiner* — Marcela M Cordero Garcia
(74) *Attorney, Agent, or Firm* — Parker Highlander PLLC

(57) ABSTRACT

Methods and compositions are provided for treating and preventing preterm labor using liposome encapsulated tocolytic agents, such as indomethacin. In certain aspects, targeted liposomes are provided that allow delivery of tocolytic agents directly to the uterus, such as by targeting to the oxytocin receptor.

15 Claims, 20 Drawing Sheets

(56) References Cited

OTHER PUBLICATIONS

International Preliminary Report on Patentability issued in International Application No. PCT/US16/67449, dated Jun. 28, 2018.
International Search Report and Written Opinion issued in International Application No. PCT/US16/67449, dated Mar. 17, 2017.
Paul, et al. "Drug delivery to the human and mouse uterus using immunoliposomes targeted to the oxytocin receptor." *American Journal of Obstetrics and Gynecology* 216.3 (2017): 283-e1.
Paul, Jonathan, Susan Hua, and Roger Smith. "A targeted drug delivery system for the uterus." *Reproductive Sciences.* vol. 22., No. 1, Suppl, p. 57A, Abstract0-003, 2015.
Refuerzo, Jerrie S., et al. "Liposomes: a nanoscate drug carrying system to prevent indomethacin passage to the fetus in a pregnant mouse model." *American Journal of Obstetrics and Gynecology* 212.4 (2015): 508-e1.
Soehngen, et al: "Encapsulation of indomethacin in liposomes provides protection against both gastric and intestinal ulceration when orally administered to rats." *Arthritis & Rheumatism: Official Journal of the American College of Rheumatology* 31.3 (1988): 414-422.
Szebeni, et al. "Hemodynamic changes induced by liposomes and liposome-encapsulated hemoglobin in pigs: a model for pseudoallergic cardiopulmonary reactions to liposomes: role of complement and inhibition by soluble CR1 and anti-C5a antibody," *Circulation* 99.17 (1999): 2302-2309.

\* cited by examiner

LIP-IND-ORA

Saline

THERAPEUTICS FOR PRETERM LABOR MANAGEMENT

The present application is a national phase application under 35 U.S.C. § 371 of International Application No. PCT/US2016/067449, filed Dec. 19, 2016, which claims the priority benefit of U.S. provisional application No. 62/269,651, filed Dec. 18, 2015, the entire contents of each of which are incorporated herein by reference.

The invention was made with government support under Grant No: R21 HD082947 awarded by the National Institutes of Health. The government has certain rights in the invention.

BACKGROUND OF THE INVENTION

1. Field of the Invention

The present invention relates generally to the fields of biology and medicine. More particularly, it concerns compositions and methods for preterm labor management.

2. Description of Related Art

Prematurity is a leading cause of perinatal morbidity and mortality affecting 12% of approximately 4 million deliveries in the United States (US). Though the etiology of preterm labor is largely unknown, it is defined as regular contractions of the uterus resulting in changes in the cervix prior to 37 weeks of pregnancy. Premature newborns are at increased risk for both acute and chronic health problems, and developmental deficiencies. Due to maternal medical conditions or complication of pregnancy, medications are frequently essential for the health of the pregnant mother and fetus(es) requiring ongoing or episodic treatment. Fetal exposure to medications most commonly occurs when free unbound drug crosses the placenta (van der Aa et al., 1998; Garland, 1998; Syme et al., 2004). Targeting therapeutics to the affected tissue and minimizing the circulating free drug fraction for placental passage can open new opportunities in the field of obstetrics.

Tocolytics remain the primary treatment for preterm labor to delay delivery. The fundamental problems with tocolytic therapies are their marginal efficacy and potential adverse effects to the fetus. Unfortunately, although highly demanded, there has been no significant improvement in tocolytic therapies for the past three decades, which can be ascribed to scant innovation in the field of drug therapies for preterm labor.

Indomethacin (IND) is the most effective tocolytic medication clinically available in the US. IND belongs to the non-steroidal anti-inflammatory drugs (NSAID) family, which acts by reducing prostaglandin production in the maternal uterus. IND freely crosses the placenta and its administration is associated with fetal adverse effects including antenatal closure of the ductus arteriosus, oligohydramnios, necrotizing enterocolitis (Major et al., 1994), and intraventricular hemorrhage (Suarez et al., 2001) both in human and animal models. Thus, there is a need for targeted tocolytic therapy to address these fundamental problems unique to pregnancy by making therapeutics function better and safer for both mother and baby.

SUMMARY OF THE INVENTION

In a first embodiment there is provided a pharmaceutical composition comprising a tocolytic agent encapsulated in a liposome. In some aspects, the tocolytic agent is an agent that crosses the placenta (when provided in an encapsulated form).

In certain aspects, the tocolytic agent comprises β2-adrenergic agonist, a calcium-channel blocker, an oxytocin receptor antagonist (ORA), prostaglandin F2α receptor inhibitor, a nitric oxide donor or a nonsteroidal anti-inflammatory drug (NSAID). In further aspects, the β2-adrenergic agonist comprises terbutaline, ritodrine, fenoterol, salbutamol, bedoradrine sulfate, MN-221, isoxsuprine, hexoprenaline or nylidrine. In specific aspects, the calcium-channel blocker comprises nifedipine or nicardipine. In some particular aspects, the ORA comprises atosiban, retosiban, barusiban or epelsiban. In certain aspects, the prostaglandin F2α receptor inhibitor comprises OBE-001, OBE-002 or PDC-31. In other aspects, the NSAID comprises indomethacin (IND), sulindac, ketorolac, celecoxib, rofecoxib or nimesulide. In further specific aspects, the liposome comprises indomethacin. In particular aspects, the nitric oxide donor comprises sildenafil, nitric oxide or nitroglycerin.

In some aspects, the tocolytic agent comprises magnesium sulfate, progesterone or ethanol. In further aspects, the liposome comprises a targeting moiety that binds to an oxytocin receptor. In certain aspects, the targeting moiety comprises an oxytocin receptor agonist or antagonist. In some aspects, the oxytocin receptor agonist is oxytocin, carbetocin, TC OT 39, WAY 267464 dihydrochloride, [Thr$^4$]-oxytocin peptide, [HO$^1$][Thr$^4$]-oxytocin peptide, [Thr$^4$,Gly$^7$]-oxytocin peptide, or [HO$^1$][Thr$^4$,Gly$^7$]-oxytocin peptide. In a specific aspect, the oxytocin receptor agonist is oxytocin. In other particular aspects, the oxytocin receptor antagonist is atosiban, retosiban, barusiban or epelsiban. In yet a further specific aspect, the oxytocin receptor antagonist is atosiban.

In still further aspects, a liposome of the embodiments comprises a targeting moiety, such a targeting moiety that targets the liposome to the uterus. For example, the targeting moiety can comprise a protein, an antibody, a peptide, an aptamer or thioaptamer. In certain aspects, the targeting moiety is conjugated to the surface of the liposome. In some aspects, the targeting moiety is conjugated to a phospholipid in the liposome. In other aspects, the targeting moiety is conjugated to a PEGylated lipid. In specific aspects, the targeting moiety is conjugated to a PEGylated phospholipid. In further particular aspects, the PEGylated phospholipid comprises 1,2-Distearoyl-sn-glycero-3-phosphoethanolamine (DSPE). In a certain aspect, the PEGylated phospholipid comprises DSPE-PEG(2000) carboxylic acid. In some aspects, the targeting moiety comprises DSPE-PEG (2000)-atosiban (see, e.g., FIG. 5B). In other aspects, the targeting moiety is conjugated by a carbodiimide crosslinker. In a specific aspect, the targeting moiety is conjugated by a 1-ethyl-3-(-3-dimethylaminopropyl) carbodiimide hydrochloride (EDAC) crosslinker.

In some aspects, the liposome comprises at least one phospholipid. In certain aspects, the liposome comprises at least a PEGylated lipid. In particular aspects, the liposome comprises at least one cationic, anionic or zwitterionic lipid. In specific aspects, the liposome comprises cholesterol.

In additional aspects, the composition comprises a plurality of liposomes having an average diameter of about 50 to 500 nm. In certain aspects, the liposomes have an average diameter of about 100 to 400 nm, 100 to 300 nm, or 100 to 200 nm. In some aspects, the tocolytic agent comprises indomethacin and the targeting moiety comprises an oxytocin receptor antagonist that is conjugated to the liposome.

A further embodiment, there is provided a composition in accordance with any of the embodiments and aspects described herein for use in treatment of a patient. In some aspects, the patient is pregnant and is entering, or at risk for entering, pre-term labor.

In yet a further embodiment, there is provided a method of treating a pregnant patient to slow or prevent preterm labor comprising administering the patient an effective amount of a tocolytic agent encapsulated in a liposome, such the pharmaceutical compositions provided herein. In certain aspects, the patient is a human patient. In other aspects, the patient is a domestic or livestock animal. In some aspects, the liposome comprises a targeting moiety that targets the liposome to the uterus. In particular aspects, the liposome comprises a targeting moiety that binds to an oxytocin receptor. In specific aspects, the tocolytic agent is an agent that crosses the placenta. In certain aspects, compositions of the embodiments are administered locally. In further aspects, the compositions are administered systemically.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
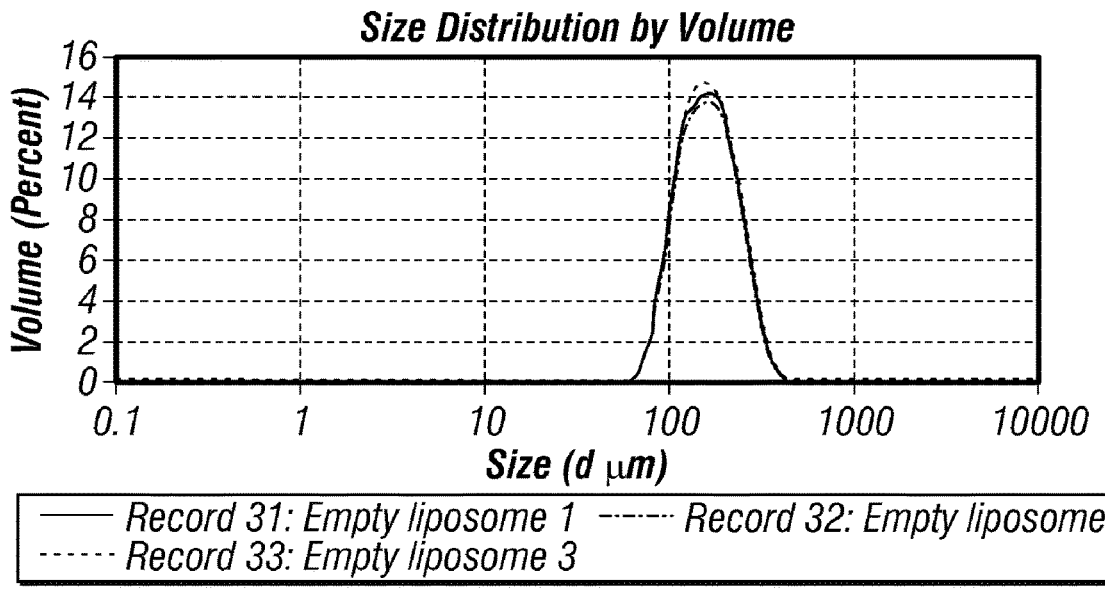
FIGS. 1A-1C: Representative graph of size distribution of (A) liposome (LIP) and (B) liposome-indomethacin (LIP-IND) using DLS and (C) Scanning Electronic Micrograph (SEM) of LIP-IND.

Preterm labor caused by uterine contractions is a major contributor to neonatal morbidity and mortality. Treatment intended to reduce uterine contractions include tocolytic agents, such as indomethacin. Unfortunately, clinically used tocolytics are frequently inefficient and cross the placenta causing fetal side effects. The embodiment of the present invention overcomes challenges associated with current technologies by providing methods and compositions for controlled delivery of tocolytic agents. For example, it has been demonstrated that by providing a tocolytic agent encapsulated in a liposome, fetal exposure to the drug can be significantly reduced. Moreover, targeted liposome nanoparticles directed to the pregnant uterus and loaded with a tocolytic agent demonstrate further improved efficacy and likewise reduce the drugs placental passage. In an exemplary method, nanoliposomes encapsulating indomethacin and decorated with clinically used oxytocin receptor antagonist, ORA, these particles (termed LIP-IND-ORA) were designed and evaluated in-vitro, ex-vivo and in-vivo. Studies herein show that the particles improve drug efficacy by increasing the fraction of the drug available to its intended site of action, while decreasing fetal exposure to the drug. LIP-IND-ORA can specifically direct the delivery of IND to the pregnant uterus, inhibit uterine contractions, and reduce preterm birth. This promising approach could open new horizons for drug development in obstetrics that could greatly impact preterm birth, which currently has no successful treatments.

I. NANOPARTICLES

As used herein, the term "nanoparticle" refers to any material having dimensions in the 1-1,000 nm range. In some embodiments, nanoparticles have dimensions in the 50-500 nm range. In particular aspects, nanoparticles are lipid-based nanoparticles including liposomes, lipid preparations and lipid-based vesicles. Lipid-based nanoparticles may be positively charged, negatively charged or neutral. In certain embodiments, the lipid-based nanoparticle is neutrally charged.

A "liposome" is a generic term encompassing a variety of uni- and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition. Liposomes provided herein include unilamellar liposomes, multilamellar liposomes and multivesicular liposomes. Liposomes provided herein may be positively charged, negatively charged or neutrally charged. In certain embodiments, the liposomes are neutral in charge.

A multilamellar liposome has multiple lipid layers separated by aqueous medium. They form spontaneously when lipids comprising phospholipids are suspended in an excess of aqueous solution. The lipid components undergo self-rearrangement before the formation of closed structures and entrap water and dissolved solutes between the lipid bilayers or within the core (Ghosh and Bachhawat, 1991). Lipophilic molecules or molecules with lipophilic regions may also dissolve in or associate with the lipid bilayer.

In specific aspects, a tocolytic agent, for example IND, is encapsulated in the aqueous interior of a liposome, interspersed within the lipid bilayer of a liposome, attached to a liposome via a linking molecule that is associated with both the liposome and the agent, entrapped in a liposome, complexed with a liposome, or the like. In further aspects, the liposome comprises a targeting agent bound or conjugated to the exterior of the liposome.

A liposome used according to the present embodiments can be made by different methods, as would be known to one of ordinary skill in the art. For example, a phospholipid (Avanti Polar Lipids, Alabaster, Ala.), such as for example the neutral phospholipid dioleoylphosphatidylcholine (DOPC), is dissolved in tert-butanol. The lipid(s) is then mixed with a therapeutic agent and/or a targeting moiety. Tween 20 is added to the lipid mixture such that Tween 20 is about 5% of the composition's weight. Excess tert-butanol is added to this mixture such that the volume of tert-butanol is at least 95%. The mixture is vortexed, frozen in a dry ice/acetone bath and lyophilized overnight. The lyophilized preparation is stored at −20° C. and can be used up to three months. When required the lyophilized liposomes are reconstituted in 0.9% saline or sterile water for injection.

Alternatively, a liposome can be prepared by mixing lipids in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25-50 mM phospholipid in sterile, pyrogen-free water, saline or a buffer by shaking until all the lipid film is resuspended. The aqueous liposomes can be then separated into aliquots, each placed in a vial, lyophilized and sealed under vacuum.

The dried lipids or lyophilized liposomes prepared as described above may be dehydrated and reconstituted in a solution of a protein or peptide and diluted to an appropriate concentration with a suitable solvent, e.g., DPBS. The mixture is then vigorously shaken in a vortex mixer. Unencapsulated additional materials, such as agents including but not limited to hormones, drugs, nucleic acid constructs, targeting moieties and the like, are removed by centrifugation at 29,000×g and the liposomal pellets washed. The washed liposomes are resuspended at an appropriate total phospholipid concentration, e.g., about 50-200 mM. The amount of additional material or active agent encapsulated can be determined in accordance with standard methods.

After determination of the amount of additional material or active agent encapsulated in the liposome preparation, the liposomes may be diluted to appropriate concentrations and stored at 4° C. until use. A pharmaceutical composition comprising the liposomes will usually include a sterile, pharmaceutically acceptable carrier or diluent, such as water or saline solution.

Additional methods for liposome preparation that may be used in the present disclosure include mechanical methods (e.g., vortex, extrusion through polycarbon filter at low/medium pressure, microfluidizer, high pressure homogenization, ultrasonic irritation, microfluidics, and bubbling of the gas), methods based on replacement of organic solvent(s) by aqueous media (e.g., removal of organic solvent(s), use of water-immiscible solvents including ether and petroleum, ethanol or tert-butanol injection method, solvent vaporization, and reverse-phase evaporation), methods based on detergent removal, gel exclusion chromatography, dialysis, and fast dilution.

In other alternative methods, liposomes can be prepared in accordance with other known laboratory procedures (e.g., see Bangham et al., 1965; Gregoriadis, 1979; Deamer and Uster, 1983; Szoka and Papahadjopoulos, 1978, each incorporated herein by reference in relevant part). Additional liposomes which may be useful with the present embodiments include cationic liposomes, for example, as described in WO02/100435A1, U.S. Pat. No. 5,962,016, U.S. Application 2004/0208921, WO03/015757A1, WO04029213A2, U.S. Pat. Nos. 5,030,453, and 6,680,068, all of which are hereby incorporated by reference in their entirety without disclaimer. A process of making liposomes is also described in WO04/002453A1. Neutral lipids can be incorporated into cationic liposomes (e.g., Farhood et al., 1995). Various neutral liposomes which may be used in certain embodiments are disclosed in U.S. Pat. No. 5,855,911, which is incorporated herein by reference. These methods differ in their respective abilities to entrap aqueous material and their respective aqueous space-to-lipid ratios.

In one embodiment, the liposomes are prepared using a microfluidics technology, such as NanoAssemblr™ (Precision NanoSystems, Inc) (described in Kastner et al., 2014; incorporated herein by reference). Nanoassemblr™ enables rapid, reproducible and scalable manufacture of homogeneous next-generation nanoparticles and liposomes (Belliveau et al., 2012; Zhigaltsev et al., 2012) using a microfluidic mixing cartridge, where lipid-containing solvent is pumped into one inlet and aqueous buffer into the other inlet. Liposome formation takes place at the interface of the solvent and aqueous streams and is based on polarity change along the chamber. The mixing is promoted by the design of the channel and channel floor groove, which enhance the controlled turbulence flow, creating an increase in the surface area of the fluid interface. The characteristics of liposome formation can be controlled via flow rates alterations of the separate streams as well the ratios of aqueous to solvent stream (Zhigaltsev et al., 2012; Balley et al., 2012). Furthermore, the system can be scaled-up by using parallelized mixing cartridges, allowing their utilization as a high throughput method (Belliveau et al., 2012).

The size of a liposome varies depending on the method of synthesis. Liposomes in the present embodiments can be a variety of sizes. In certain embodiments, the liposomes are small, e.g., less than about 500 nm, 200, nm about 90 nm, about 80 nm, about 70 nm, about 60 nm, or less than about 50 nm in external diameter. For example, in general, after the incorporation of a drug or targeting moiety, a liposome for use according to the present embodiments comprises a size of about 50 to 500 nm. Such liposome formulations may also be defined by particle charge (zeta potential) and/or optical density (OD). In preparing such liposomes, any protocol described herein, or as would be known to one of ordinary skill in the art may be used. Additional non-limiting examples of preparing liposomes are described in U.S. Pat. Nos. 4,728,578, 4,728,575, 4,737,323, 4,533,254, 4,162,282, 4,310,505, and 4,921,706; International Applications PCT/US85/01161 and PCT/US89/05040; U.K. Patent Application GB 2193095 A; Mayer et al., 1986; Hope et al., 1985; Mayhew et al. 1987; Mayhew et al., 1984; Cheng et al., 1987; and Liposome Technology, 1984, each incorporated herein by reference).

In certain embodiments, the lipid based nanoparticle is a neutral liposome (e.g., a DOPC liposome). "Neutral liposomes" or "non-charged liposomes", as used herein, are defined as liposomes having one or more lipid components that yield an essentially-neutral, net charge (substantially non-charged). By "essentially neutral" or "essentially non-charged", it is meant that few, if any, lipid components within a given population (e.g., a population of liposomes) include a charge that is not canceled by an opposite charge of another component (i.e., fewer than 10% of components include a non-canceled charge, more preferably fewer than 5%, and most preferably fewer than 1%). In certain embodiments, neutral liposomes may include mostly lipids and/or phospholipids that are themselves neutral under physiological conditions (i.e., at about pH 7).

Liposomes and/or lipid-based nanoparticles of the present embodiments may comprise a phospholipid. In certain embodiments, a single kind of phospholipid may be used in the creation of liposomes (e.g., a neutral phospholipid, such as DOPC, may be used to generate neutral liposomes). In other embodiments, more than one kind of phospholipid may be used to create liposomes.

Phospholipids include, for example, phosphatidylcholines, phosphatidylglycerols, and phosphatidylethanolamines; because phosphatidylethanolamines and phosphatidyl cholines are non-charged under physiological conditions (i.e., at about pH 7), these compounds may be particularly useful for generating neutral liposomes. In certain embodiments, the phospholipid DOPC is used to produce non-charged liposomes. In certain embodiments, a lipid that is not a phospholipid (e.g., a cholesterol) may be used.

Phospholipids include that may be used in liposomes of the embodiments include, without limitation, glycerophospholipids and certain sphingolipids. Phospholipids include, but are not limited to, dioleoylphosphatidylycholine ("DOPC"), egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), distearoyl sphingomyelin ("DSSP"), distearoylphophatidylethanolamine ("DSPC"), dioleoylphosphatidylglycerol ("DOPG"), dimyristoyl phosphatidic acid ("DMPA"), dipalmitoyl phosphatidic acid ("DPPA"), dimyristoyl phosphatidylethanolamine ("DMPE"), dipalmitoyl phosphatidylethanolamine ("DPPE"), dimyristoyl phosphatidylserine ("DMPS"), dipalmitoyl phosphatidylserine ("DPPS"), brain phosphatidylserine ("BPS"), brain sphingomyelin ("BSP"), dipalmitoyl sphingomyelin ("DPSP"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), dioleoylphosphatidylethanolamine ("DOPE"), 1-palmitoyl-2-oleoyl-sn-glycero-3-phosphocholine ("POPC"), palmitoyloeoyl palmitoleoyl phosphatidylethanolamine ("POPE"), lysophosphatidylcholine, lysophosphatidylethanolamine, and dilinoleoylphosphatidylcholine.

Phospholipids may be from natural or synthetic sources. However, phospholipids from natural sources, such as egg or soybean phosphatidylcholine, brain phosphatidic acid, brain or plant phosphatidylinositol, heart cardiolipin and plant or bacterial phosphatidylethanolamine are not used, in certain embodiments, as the primary phosphatide (i.e., constituting 50% or more of the total phosphatide composition) because this may result in instability and leakiness of the resulting liposomes. In certain aspects, the phospholipid is not a phospholipid from a natural source. For example, the phospholipid, in some aspects, is not from a soy bean extract.

II. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 1B:
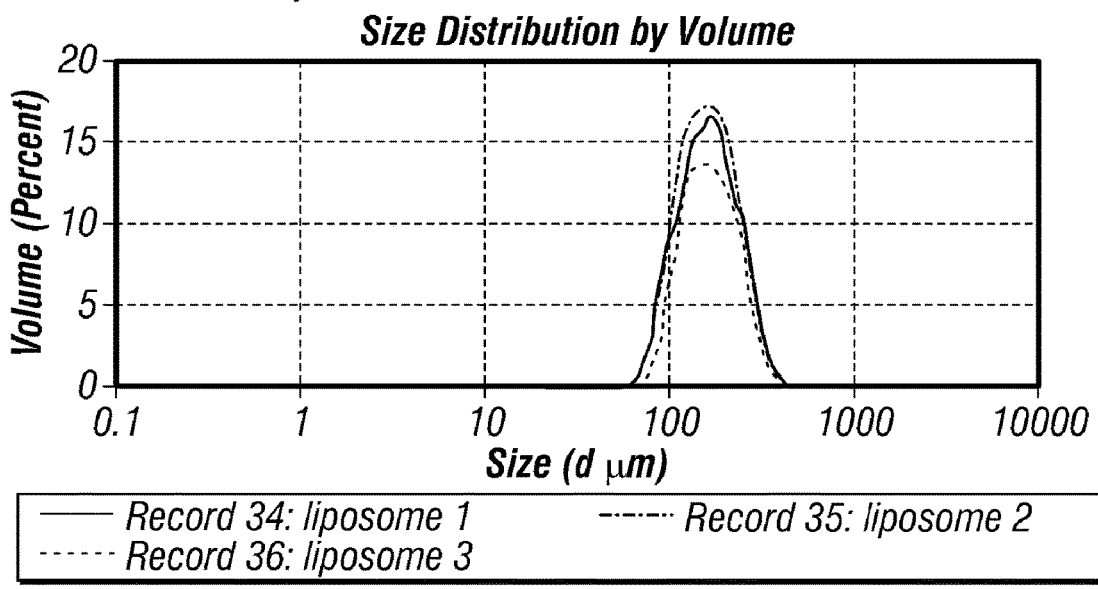
Figure 1C:
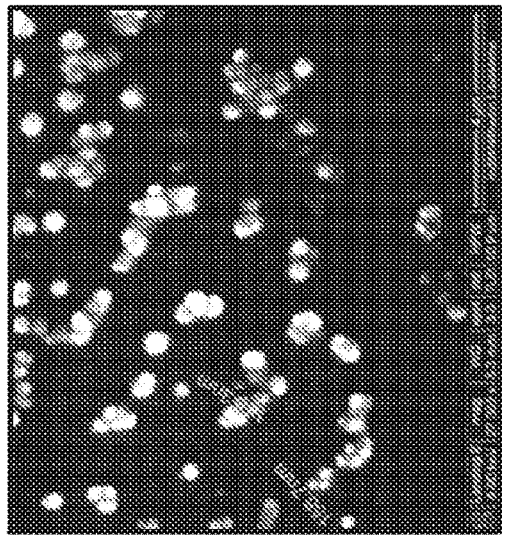

Liposome (lip) Prevents the Transfer of Indomethacin Across the Placenta to the Fetus To determine whether liposomes (LIP) could prevent the transfer of indomethacin (IND) across the placenta to the fetus while preserving its pharmacological activity, multilamellar LIP were designed with a 150-200 nm size, fluorescently labeled and loaded with IND (LIP-IND). Characterizations of the liposomes by DLS and SEM showed that the nanoparticles appear as uniform, spherical vesicles of ~150-170 diameter (FIG. 1). When the size distribution of five separately prepared batches of IND and LIP-IND was evaluated, the average values were 159.8±1.1 nm (polydispersity index, PDI<0.083) for LIP and 164.4±4.7 (PDI: 0.069) for LIP-IND. The low PDI (<0.1) values point towards the homogeneity of the formed phospholipid nanovesicles. Quantitative analysis of the drug revealed that IND encapsulation efficiency in the liposomes was 93%. To enable the biodistribution in the tissues analysis, LIP and IND-LIP were tagged with red fluorescent dye.

TABLE 1

Indomethacin level normalized per weight in the uterus, placenta and fetus.

|  | Uterus$^{NS}$ | Placenta$^{NS}$ | Fetus* |
|---|---|---|---|
| IND | 236.7 ± 21.6 | 649.7 ± 78.4 | 81.3 ± 24.7 |
| LIP-IND | 318.7 ± 54.2 | 937.8 ± 513.0 | 10.7 ± 17.1 |

IND: indomethacin,
LIP-IND: liposome-indomethacin.
Indomethacin levels are ng/g expressed as mean ± sem.
NS—Non-significant (IND vs. LIP-IND).
*p = 0.041 (IND vs. LIP-IND).

Figure 2:
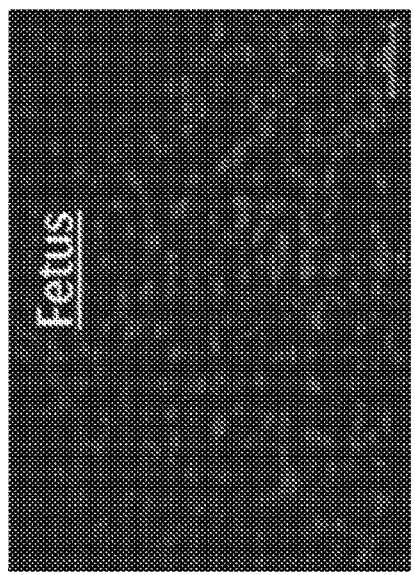
FIG. 2: LIP-IND localization in uterus, placenta and fetus as detected by fluorescent microscopy. High LIP-IND localization is observed in the uterus, a low level of localization in the placenta, and no localization in the fetus is detected by fluorescent miscroscopy.
Figure 2:
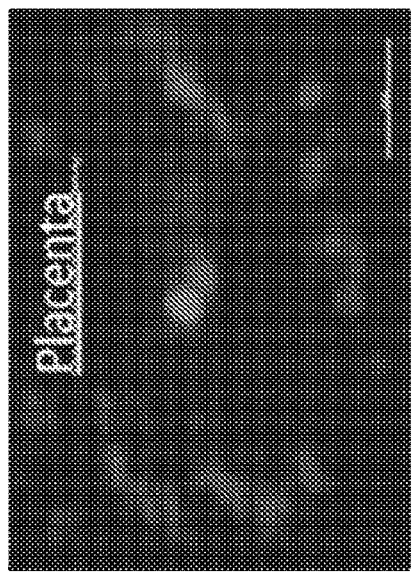
Figure 2:
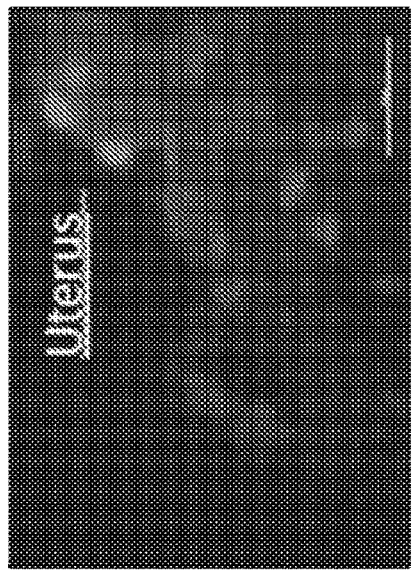
Figure 3:
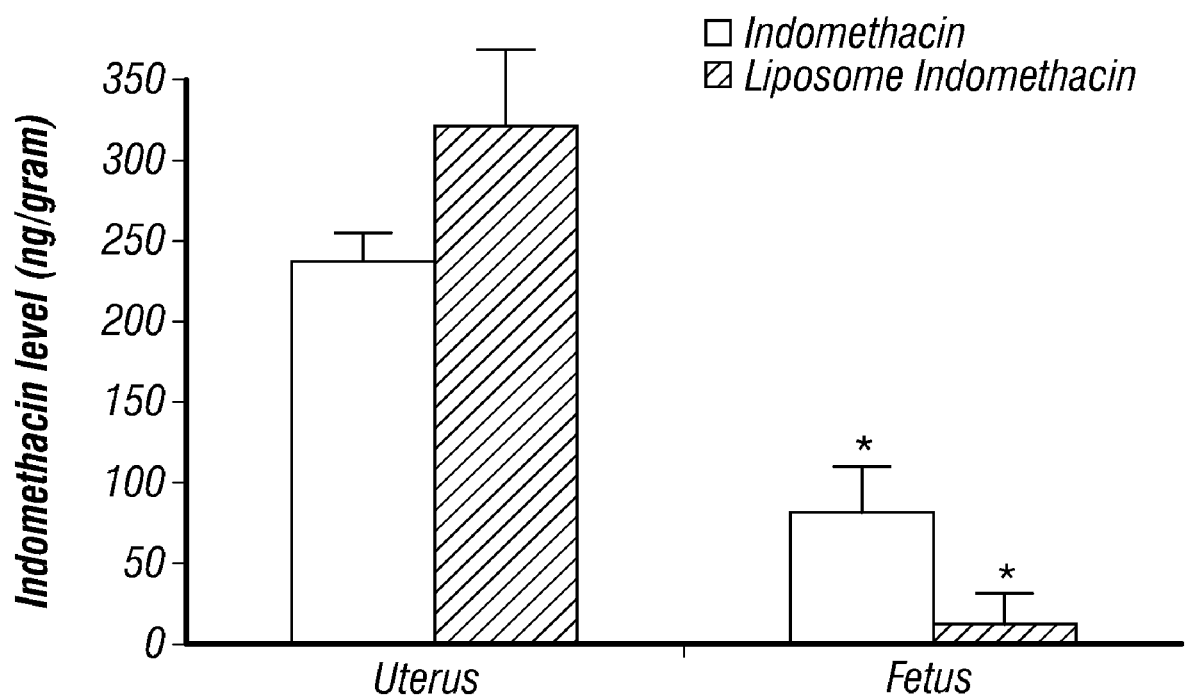
FIG. 3: Indomethacin levels within the uterus and fetus four hours following the administration of indomethacin (IND) and liposome-indomethacin (LIP-IND).

The qualitative assessment of LIP-IND distribution revealed that the system was primarily confined within the uterus, minimally detected within the placenta and absent in the fetus as shown in FIG. 2. Quantitatively, the LIP-IND brightness values were significantly higher in the uterus of animals given LIP compared to placenta and fetus, (uterus: 15.3±5.4 vs. placenta: 3.0±3.5 vs. fetus: 4.4±2.5, p=0.009). The LIP-IND system resulted in significantly lower IND levels in the fetus compared to IND alone, (LIP-IND: 10.7±17.1 ng/g vs. IND: 81.3±24.7 ng/g, p=0.041) as described in Table 1 and depicted in FIG. 3.

Figure 4:
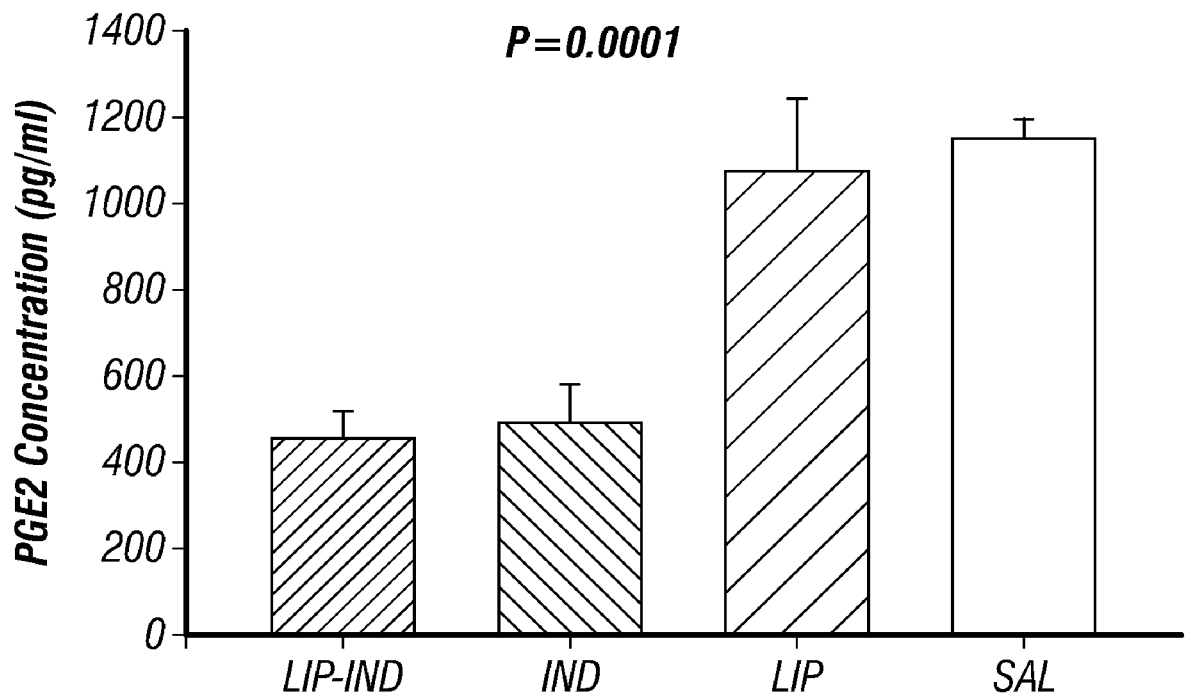
FIG. 4: Prostaglandin E2 (PGE2) levels within the uterine tissue four hours following the administration of indomethacin (IND) and liposome-indomethacin (LIP-IND).
Figure 5A:
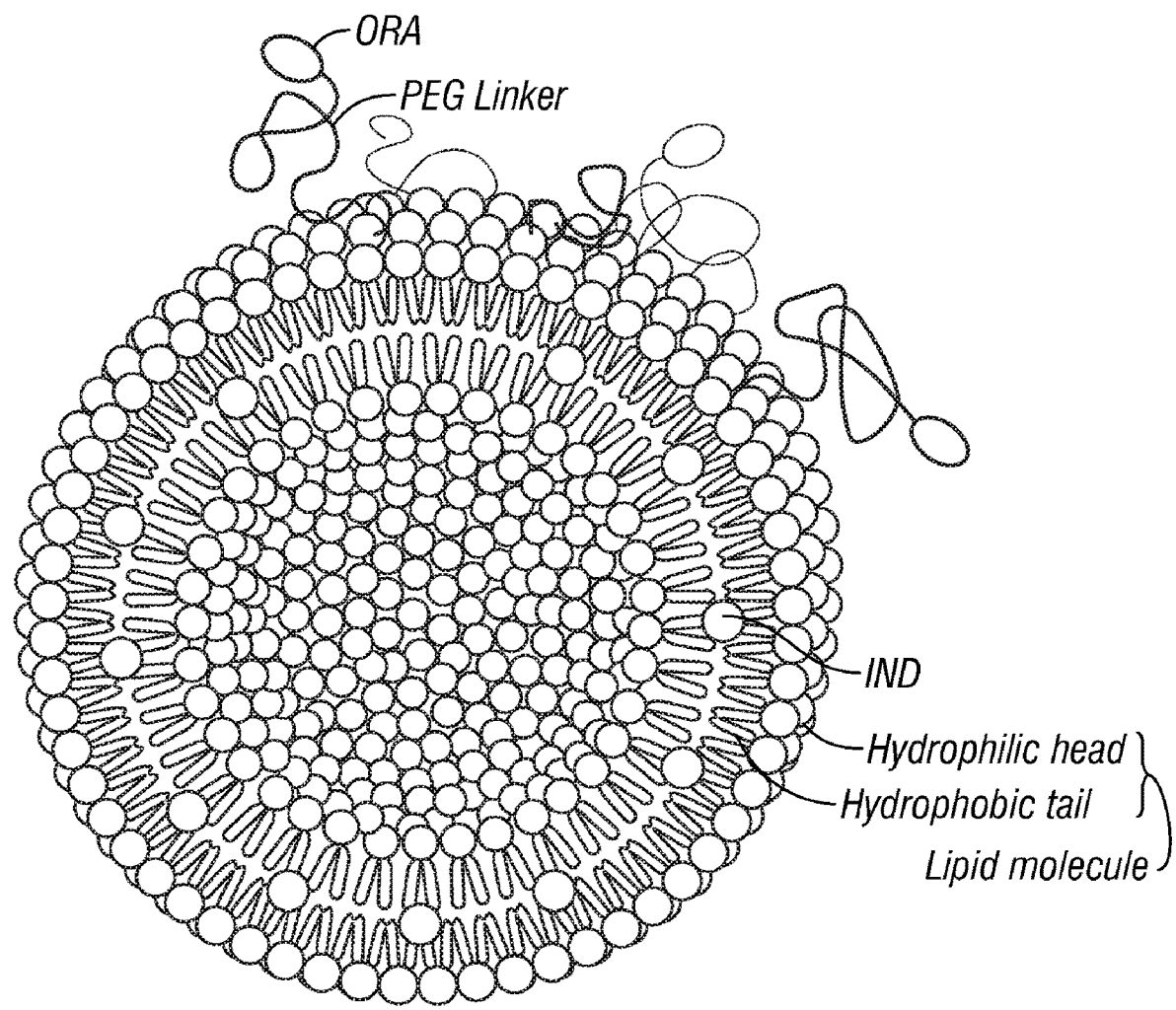
FIGS. 5A-5C: Schematic presentation of the liposome with indomethacin and oxytocin receptor antagonist, Atosiban (LIP-IND-ORA) design. (A) Illustration of LIP-IND-ORA structure and (B) Schematic of ORA conjugation to the LIP membrane. (C) Schematics of the LIP-IND-ORA mechanism of action: (1-2) binding to the oxytocin receptor expressed on the pregnant uterus and directing IND (small white circles) specifically to the uterus (3) thereby improving the tocolytic efficacy of indomethacin while reducing its placental passage.
Figure 5B:
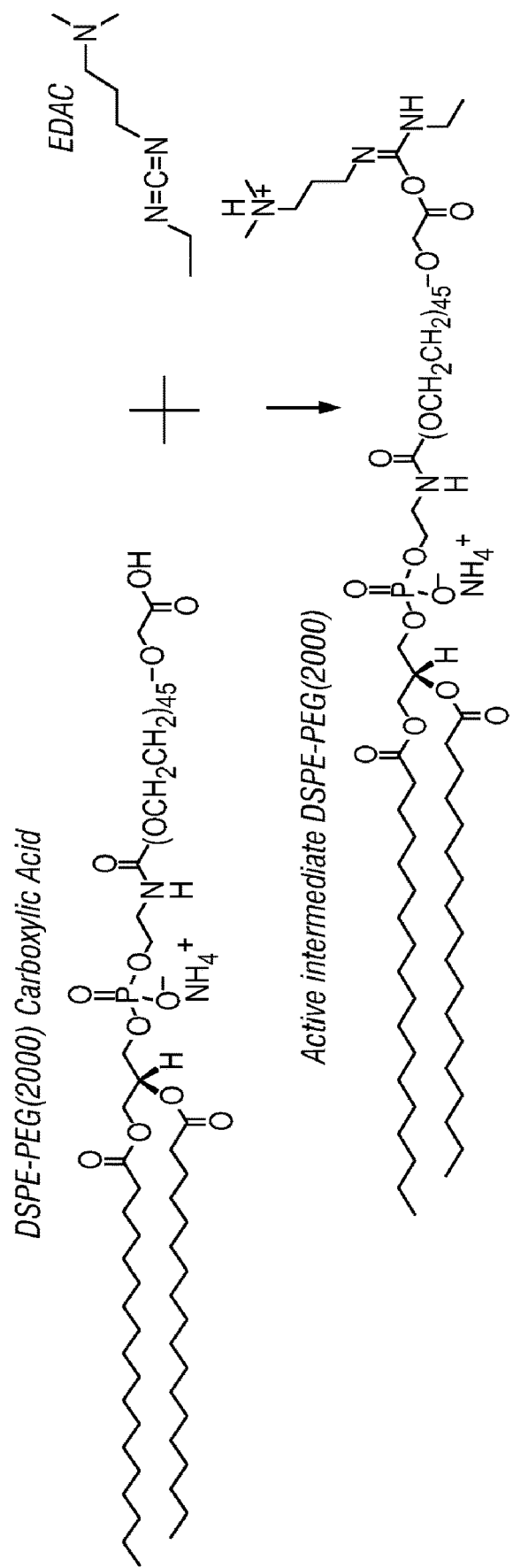
Figure 5B:
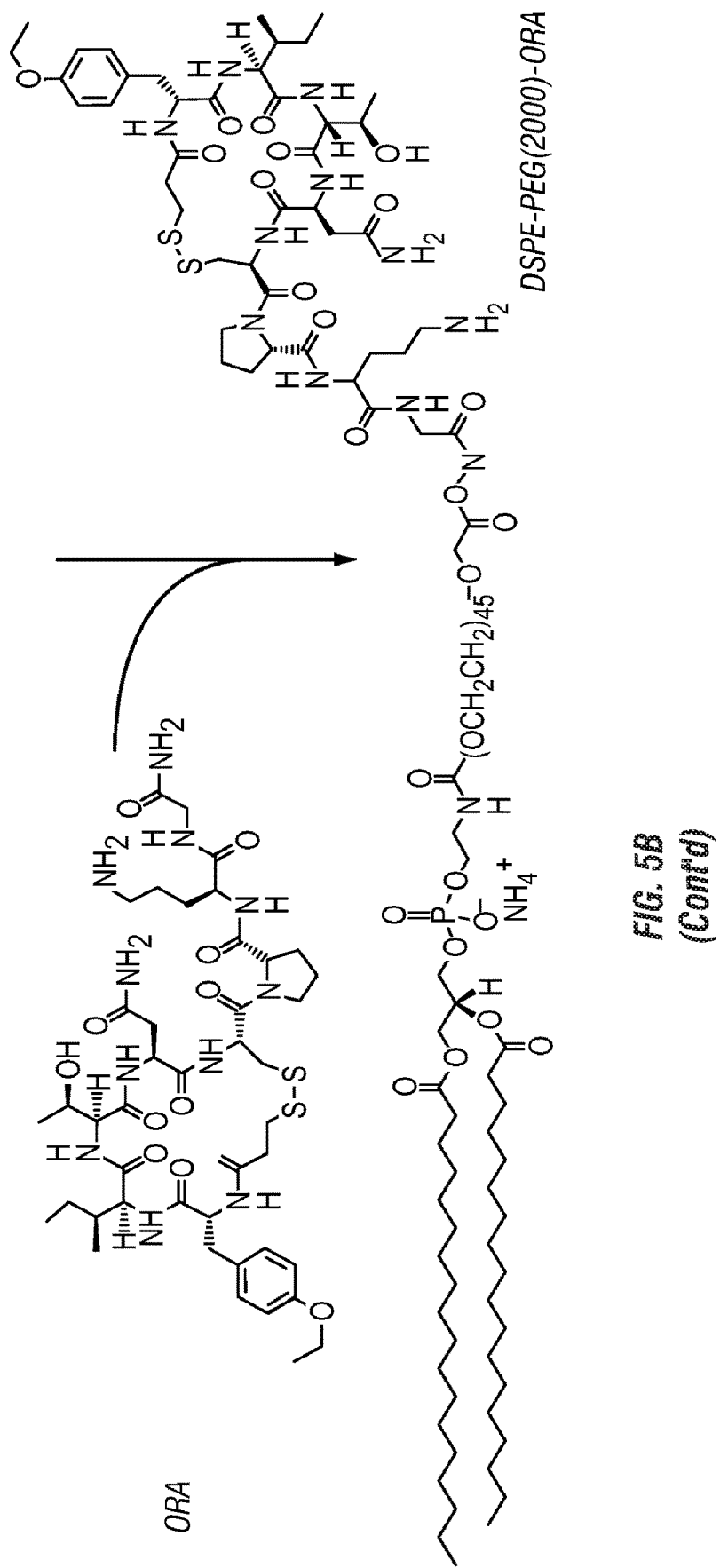
Figure 5C:
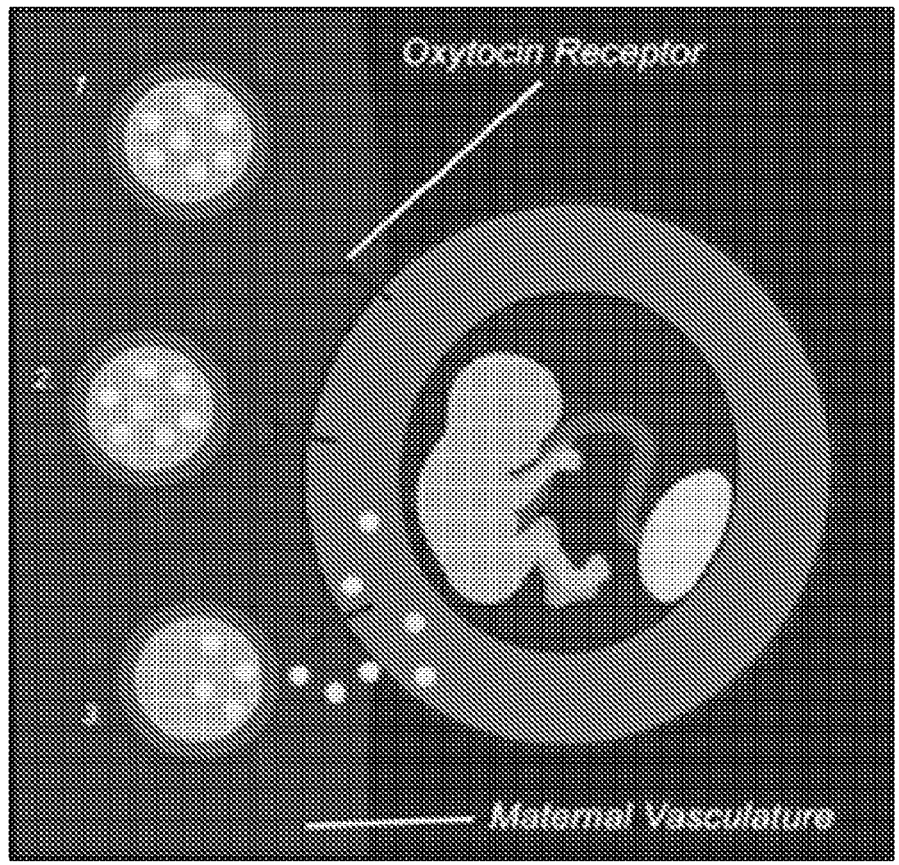

To evaluate the pharmacological effect of IND administered from LIP-IND, the levels of PGE2, were detected in the uterus. PGE2 levels were significantly reduced in the uterus of animals given LIP-IND and IND compared to LIP and SAL, (LIP-IND: 457.5±64.0 pg/mL vs. IND: 493.3±89.0 pg/mL vs. LIP: 1066.0±171.0 pg/mL vs. SAL: 1142.0±52.0 pg/mL, p=0.0001) as described in FIG. 4.

In a pregnant mouse model, LIP localized within the uterus and did not cross the placenta to the fetus. The percent of IND within the fetus was reduced 7.6-fold while encapsulated within the LIP and the PG production inhibitory effects of indomethacin were maintained.

In summary, in a pregnant mouse model, LIP-IND were not detected within the fetus and were localized within the uterus. The LIP-IND system reduced the drug levels within the fetus by 7.6-fold, yet, maintained its pharmacologic effects as demonstrated by significantly reduced PGE2 levels in the uterus. Thus, LIP provide a novel therapeutic approach to correct the primary clinical limitation of indomethacin by reducing placental passage to the fetus.

Example 2

Targeted Delivery of LIP-IND to the Pregnant Uterus

Liposome design and fabrication. To achieve active targeting of the LIP-IND system to the uterus, a new method was developed, which involved conjugating clinically used ORA to the liposome's surface. Liposomes loaded with IND and decorated with a clinically available oxytocin receptor antagonist (Flenady et al., 2014) (ORA) on its surface were fabricated into LIP-IND-ORA, as schematically presented in FIG. 5. Oxytocin receptors are specifically expressed on the pregnant uterus. Accordingly, the LIP-IND-ORA were evaluated to determine their ability to specifically direct the delivery of IND to the pregnant uterus, inhibit uterine contractions, and reduce preterm birth.

For this purpose, the liposomes were engineered to include phospholipids with a spacer and carboxylic group (PEG-DSPE), which can react with the amino group of the ORA using a post-insertion technique. Various concentrations of the constituents were tested. Among the evaluated systems, 3% PEG-DSPE was found to be the most efficient in ORA conjugation (51.8% conjugation efficiency as normalized to the molar concentration of PEG-DSPE). The resulting LIP-IND-ORA nanoliposomes are 124.2±0.7 nm in size, possess negative zeta potential of −21.2±0.4 mV and 93% IND loading efficiency. The addition of ORA to LIP-IND did not alter the drug encapsulation and fluorescent properties of the nanoparticles.

Figure 6A:
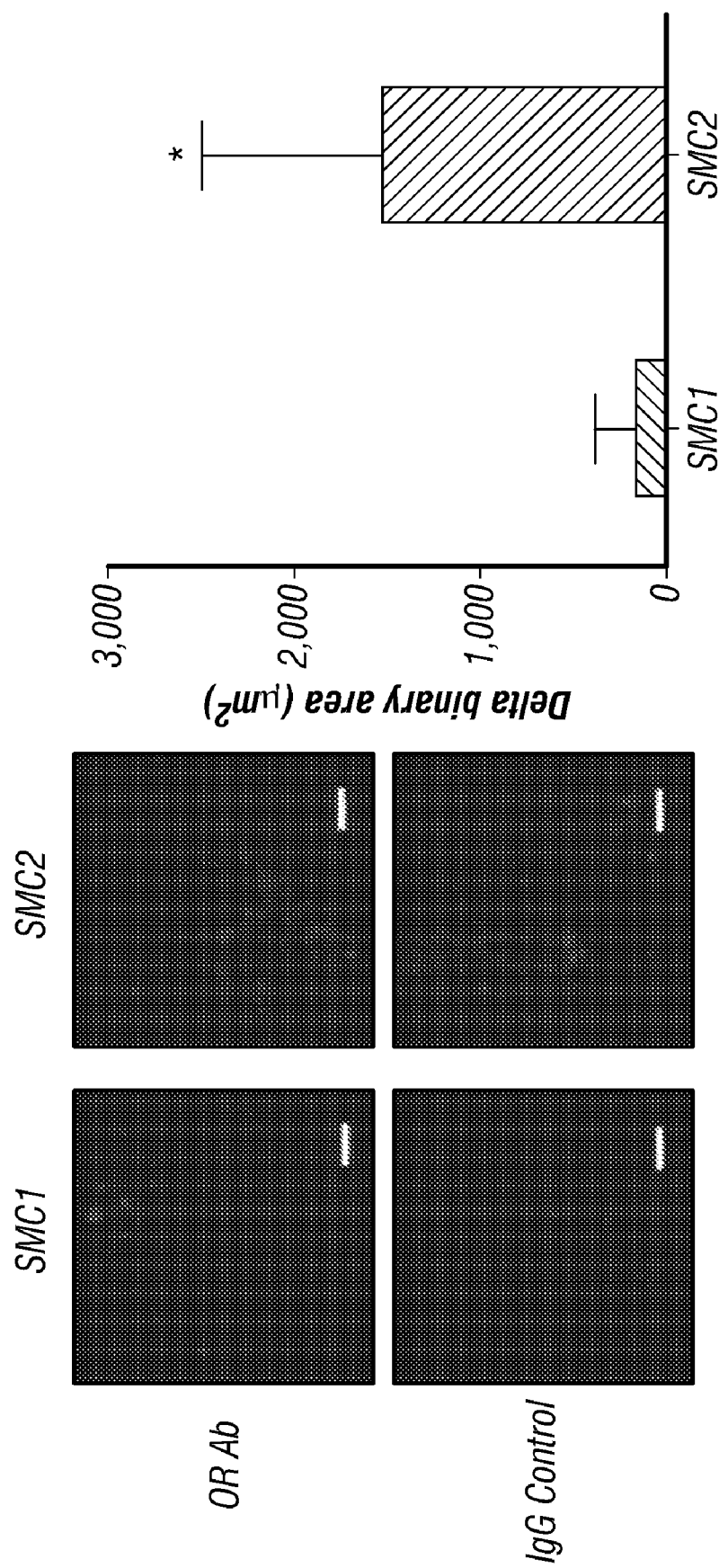
FIGS. 6A-6E: In vitro characterization of oxytocin receptor (OR) expression and correlated liposome targeting efficiency. The in vitro experiments were conducted in primary smooth muscle cells SMC1 and SMC2 isolated from pregnant mice (A-C), and in human smooth muscle cell lines SMC-A and SMC-B (D-E). OR expression was verified by immunofluorescence staining with OR antibody (OR-Ab) and analyzed via confocal microscopy (A, D), using IgG staining as a negative control. Liposome targeting specificity was analyzed via confocal microscopy (B, E), as well as via flow cytometry (C). All the images were analyzed and quantified using NIS-elements. Mean±SEM, n=9. Scale bar=50 µm. *p-value<0.05, **p-value<0.01 compared to IgG control (A,D) or to untargeted liposome (B,E).
Figure 6B:
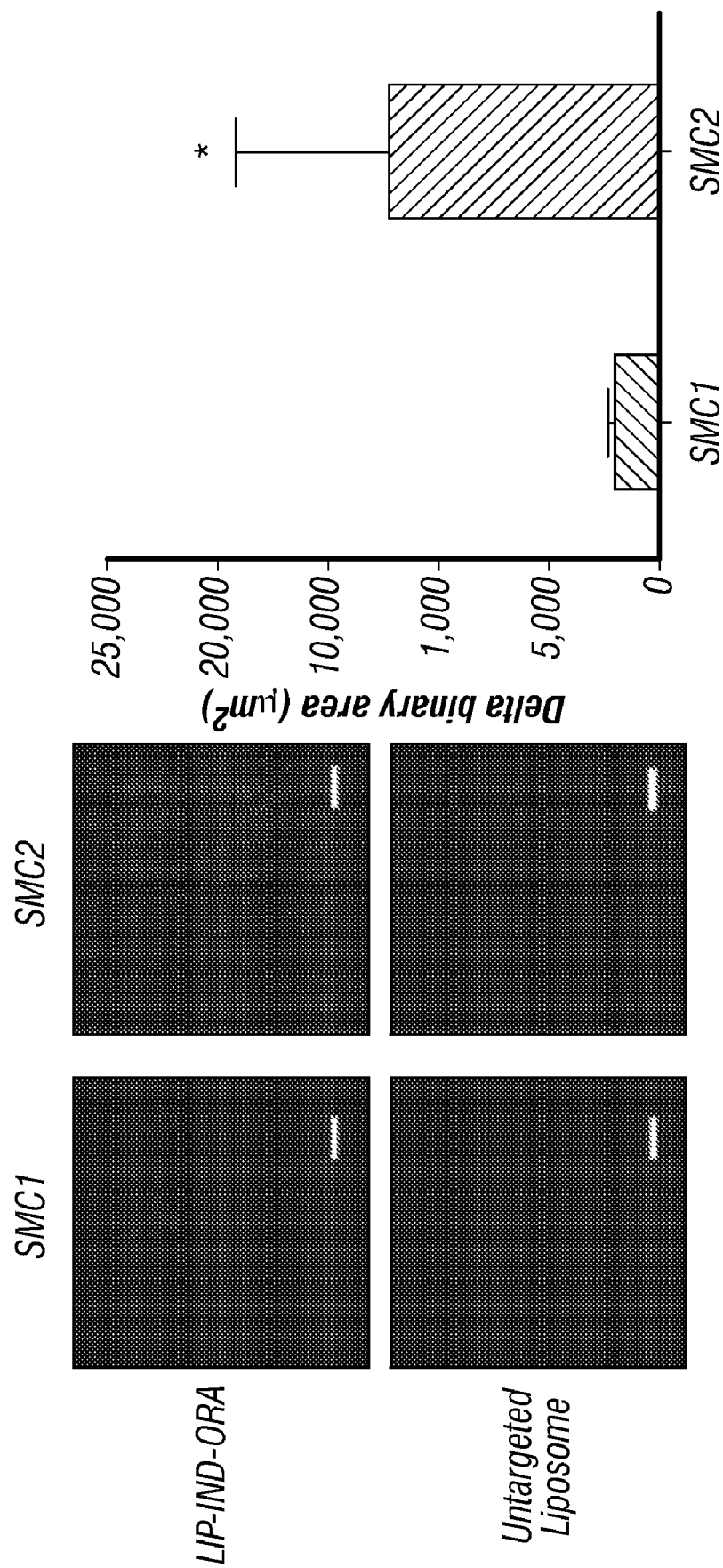
Figure 6C:
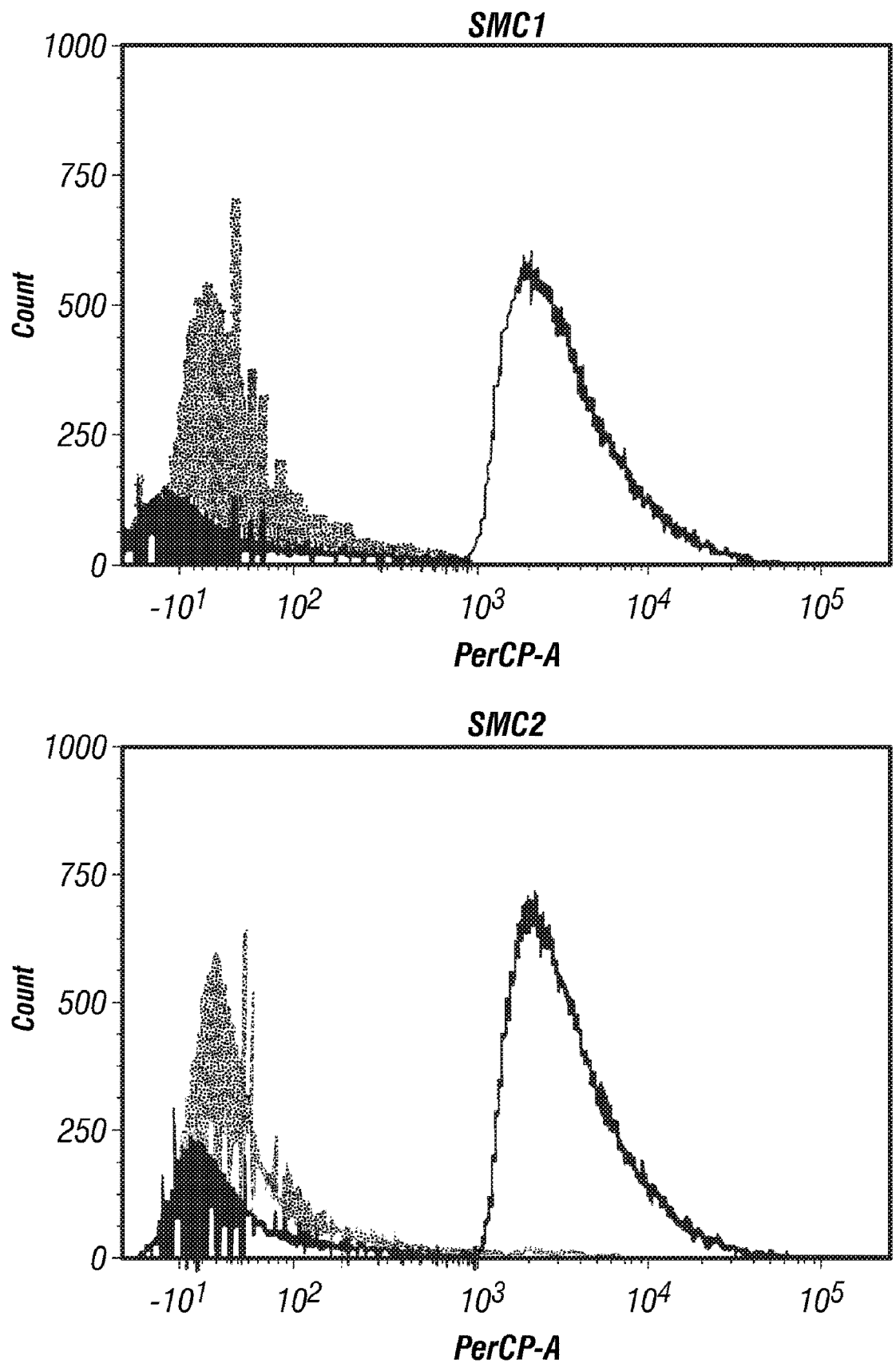

Targeting efficiency in vitro. The expression level of the oxytocin receptor (OR) was determined using immunofluorescence in smooth muscle cells (SMC) isolated from two pregnant mice (hence SMC1 and SMC2) (FIG. 6A). In both cases, the unspecific binding was tested using an isotypic IgG antibody. Both cells expressed OR, while SMC2 had four-times higher expression levels as compared to SMC1. The same trend was seen when the cells are incubated with fluorescently labeled targeted LIP-IND-ORA vs. untargeted liposomes (FIG. 6B). In both primary smooth muscle cells, LIP-IND-ORA enabled better attachment and retention when compared to untargeted liposomes. In terms of the targeting efficiency, LIP-IND-ORA attached eight-times more efficiently to SMC2 cells than to SMC1, which is in line with OR expression levels. The results were also confirmed via flow cytometry (FIG. 2C), where a significant increase in cells associated with LIP-IND-ORA was observed as compared to untargeted liposomes.

Figure 6D:
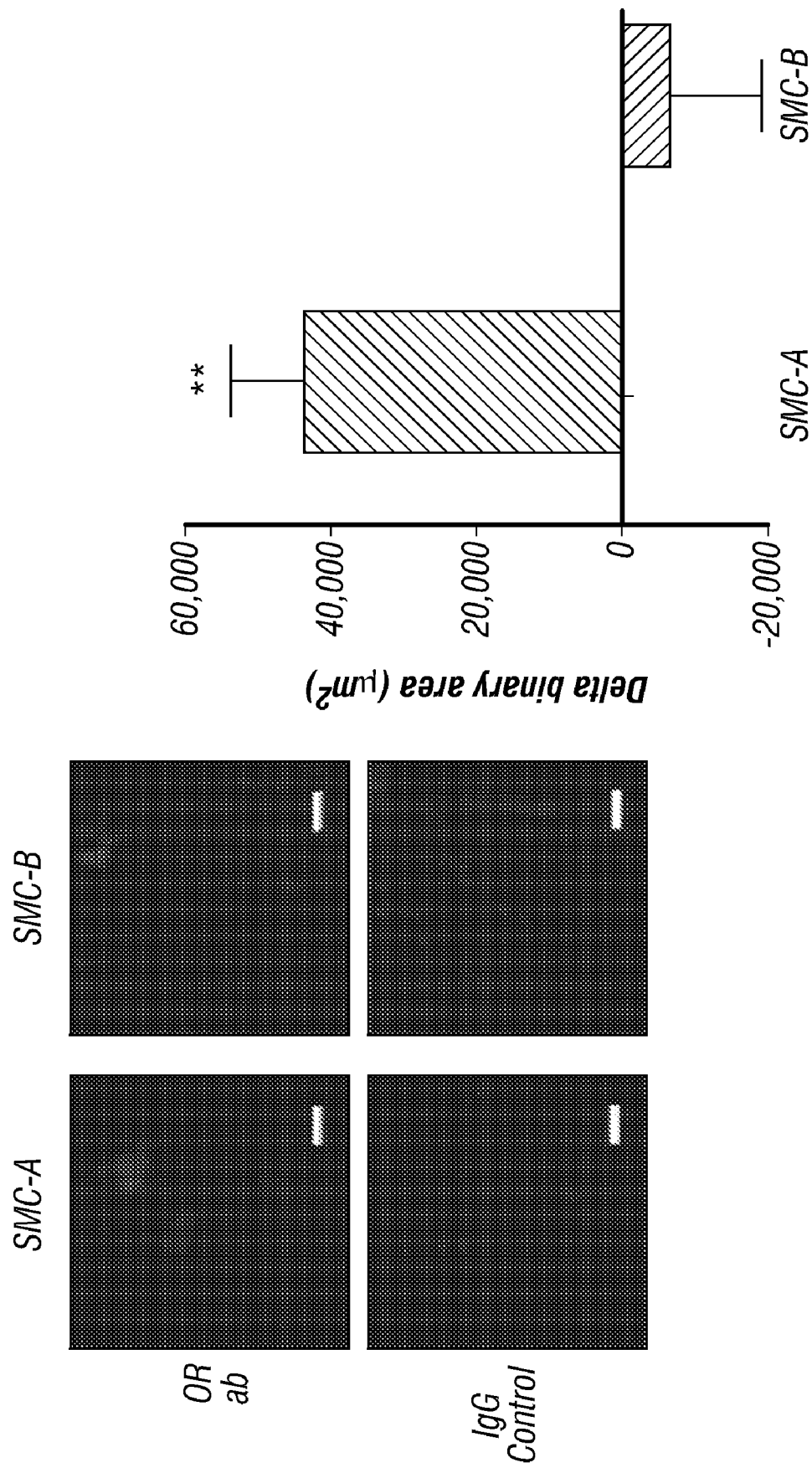
Figure 6E:
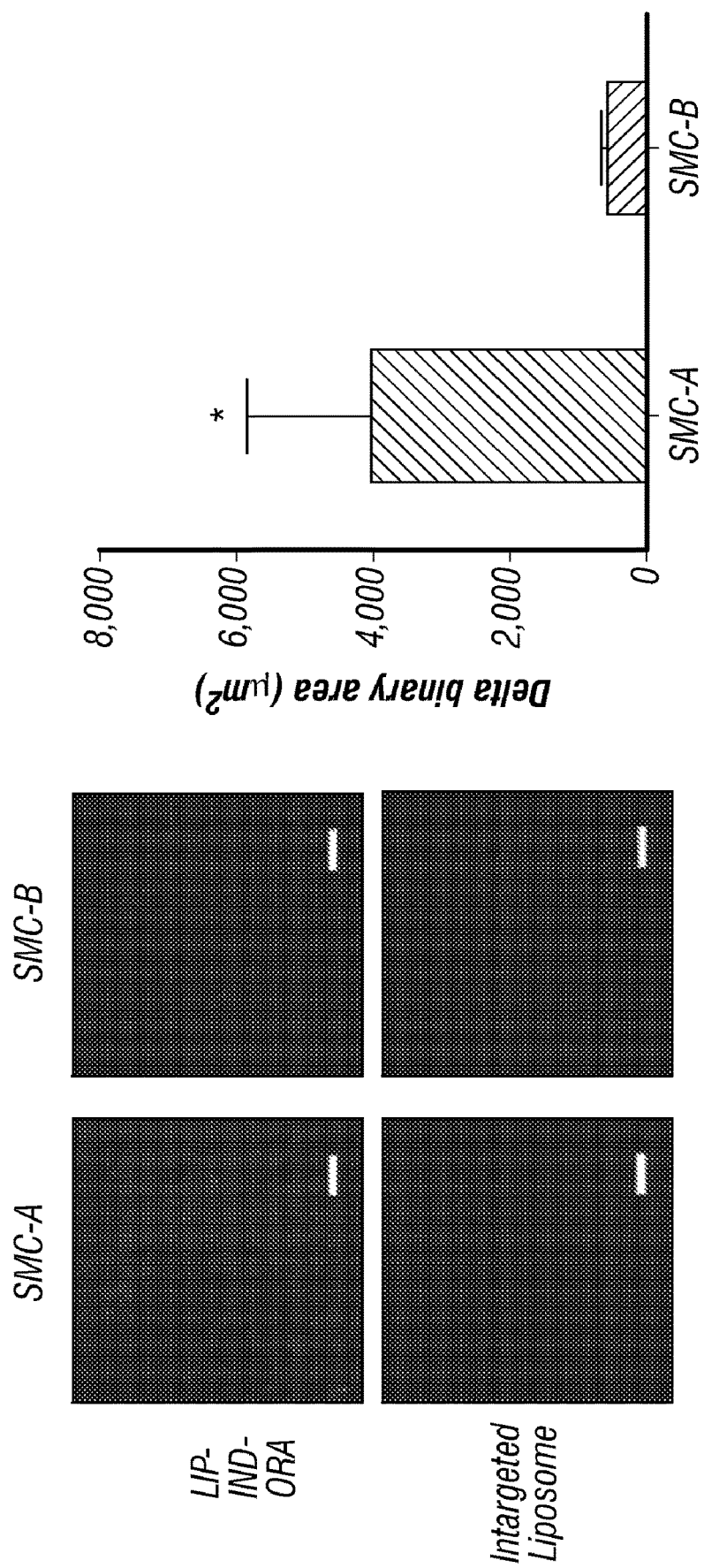

Further analysis tested an association of LIP-IND-ORA vs. untargeted liposomes with two human uterine SMC samples (SMC-A and SMC-B). The results showed a significant increase of liposome accumulation when ORA targeting is in place by 5-fold and 23-fold, for SMC-A and SMC-B, respectively (FIGS. 6D and 6E). These findings confirm that OR can be successfully targeted to murine and human uterine SMC with this system.

Figure 7A:
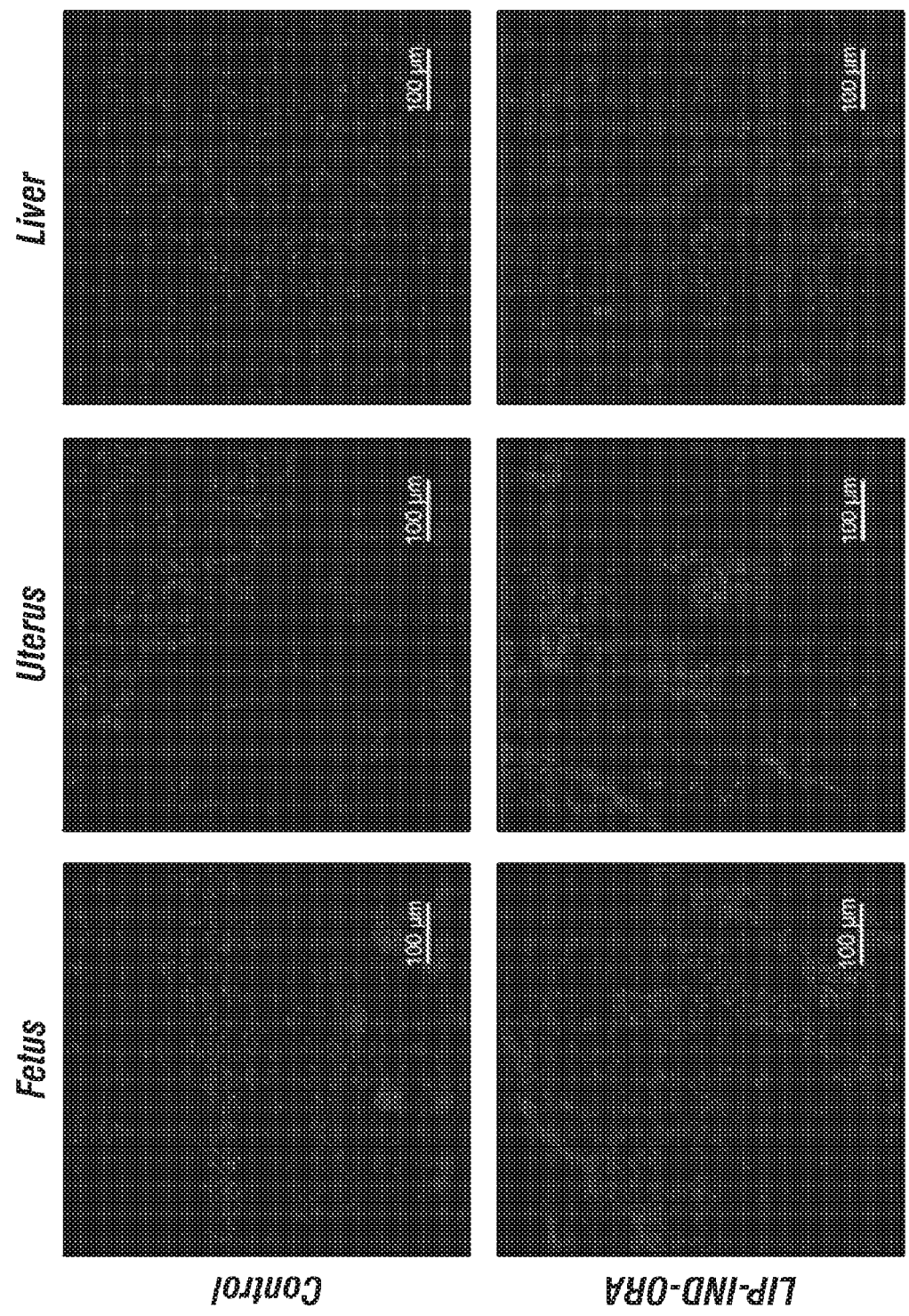
FIGS. 7A-7D: Biodistribution of LIP-IND-ORA components in vivo in pregnant mice. (A) Qualitative analysis of LIP-IND-ORA tissue distribution in the maternal uterus and liver, and in the fetus of pregnant mice. LIP-IND-ORA antibody staining is observed in the lower middle panel (LIP-IND-ORA in Uterus). (B) Additional images of fetuses of mice injected with LIP-IND-ORA vs. SAL. LIP-IND-ORA were fluorescently labeled with lissamin rhodamin, and the samples were counterstained with DAPI. The absence of lissamin rhodamin fluorescence in all panels proves the lack of penetration of the liposomes to the fetus. (C) Quantification of the LIP-IND-ORA fluorescent signal in the tissues normalized to tissue auto-fluorescence using NIS elements. Quantitative biodistribution of liposome was obtained from at least 9 randomly selected fields per mouse of each organ. (D) IND concentrations in the maternal uterus and fetus were determined by LC-MS/MS analysis. Mean±SEM, n=6.*p-value<0.05, **p-value<0.01 to fetus (C) or to levels of IND when the free drug was administered (D).
Figure 7B:
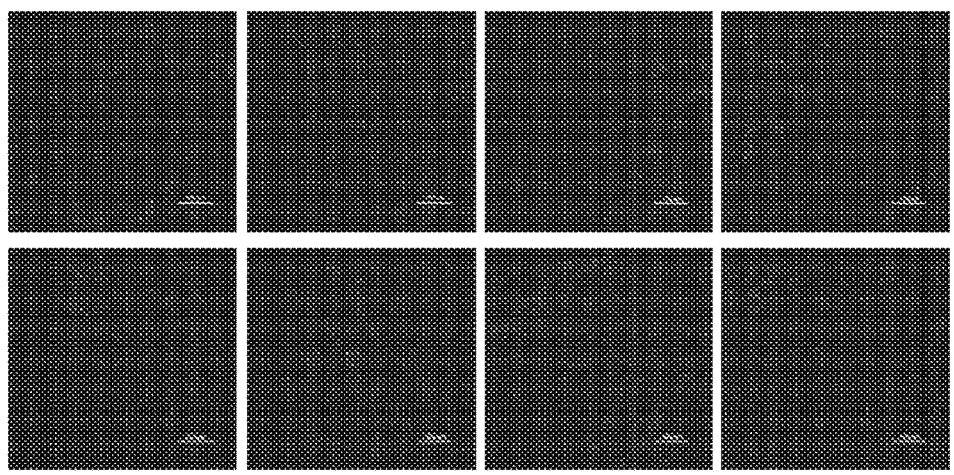
Figure 7B:
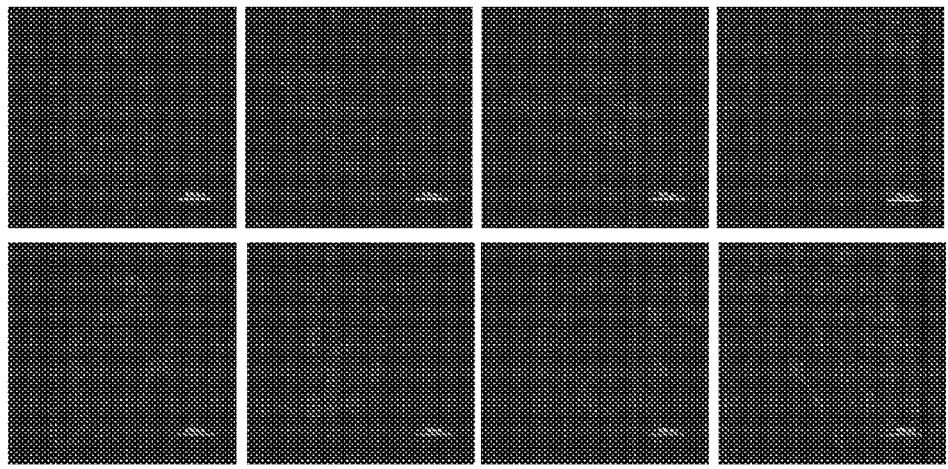
Figure 7C:
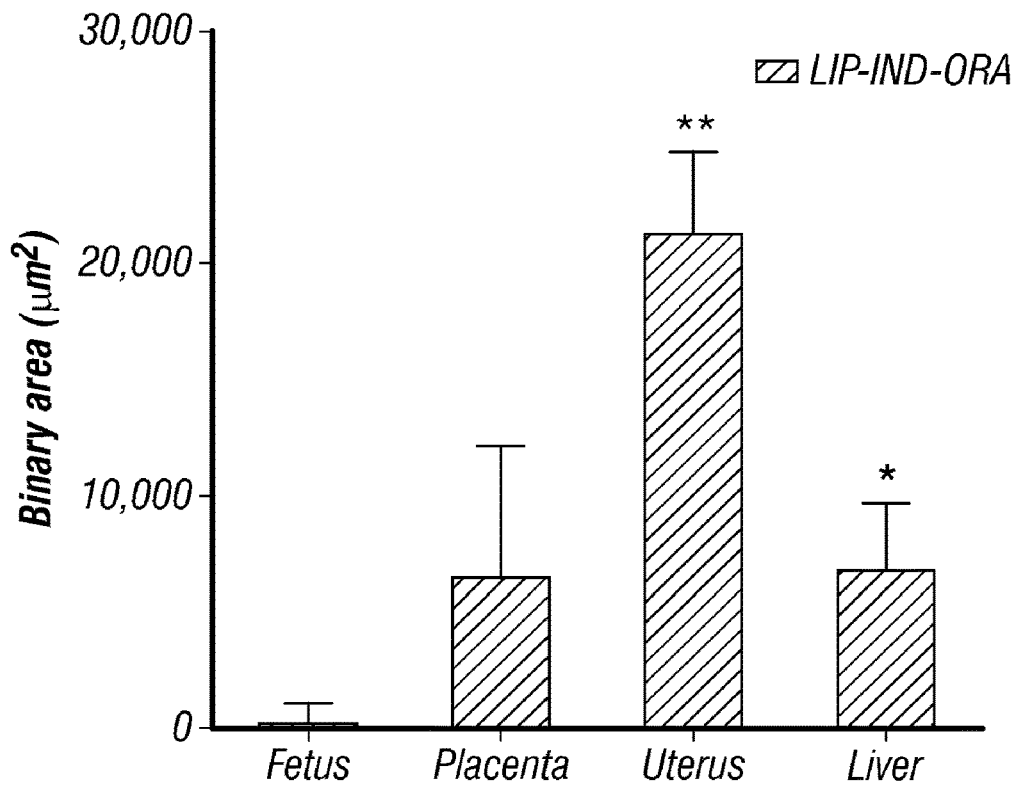

Biodistribution study in vivo. To demonstrate that targeted LIP-IND-ORA system would minimize the placental passage and deliver IND to the pregnant uterus, the biodistribution of the targeted LIP-IND-ORA system in vivo was evaluated using fluorescent microscopy of maternal and fetal tissues for tagged LIP-IND-ORA and analysis of IND by HPLC-MS/MS. Fluorescent microscopy was utilized to assess liposome localization to the uterine and fetal tissue. It is known that nanoparticles tend to accumulate in the liver (the major organ of reticulo-endothelial system) the accumulations of the LIP-IND-ORA system and IND in the liver were also measured. Based on the fluorescent microscopy assessment of the tissues, the strongest signal of the system was in the uterus of the pregnant mice. LIP-IND-ORA was primarily confined within the uterus, minimally detected within the liver and placenta, and absent in the fetus as shown in FIGS. 7A and 7B. Quantitatively, the binary area of fluorescent signal associated with LIP-IND-ORA was more than three times higher in the uterus of animals given LIP-IND-ORA compared to that in liver, placenta or the fetus, (uterus: 21,243±3,502; liver: 6,768±2,919; fetus: 168±934 p$\mu$m2, p<0.05) [n=6 per group, mean±SEM].

Figure 7D:
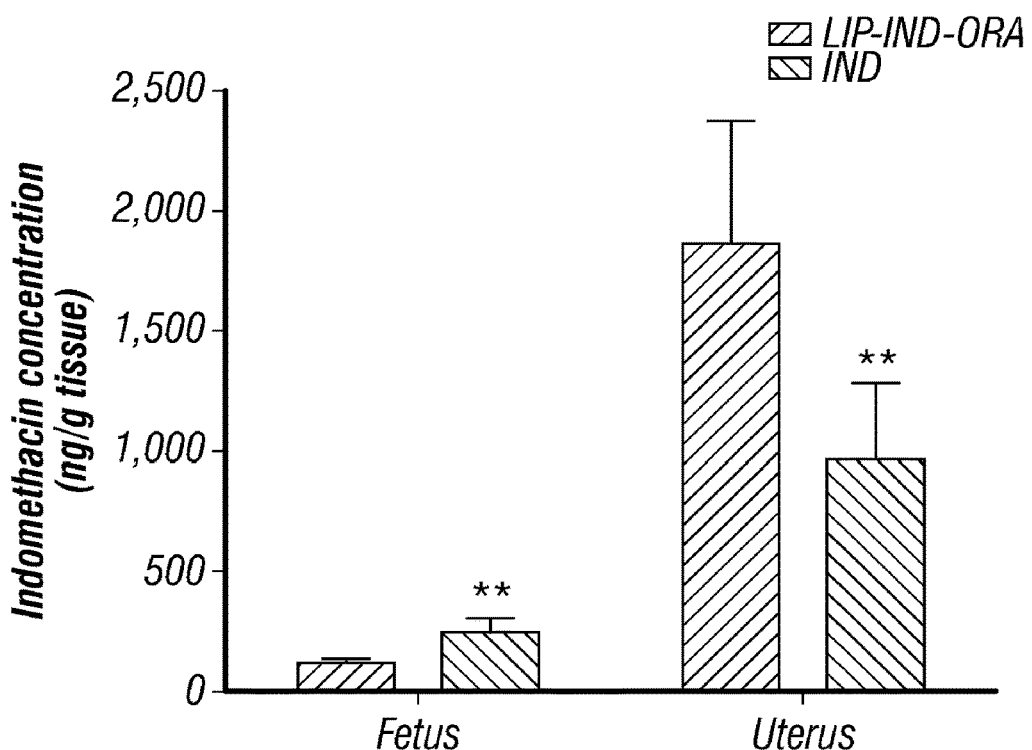

To assess reduction of placental passage of the drug when delivered using the LIP-IND-ORA system, the concentrations of IND were measured in both uterine and fetal tissue by liquid chromatography-mass spectrometry (LC-MS/MS). The concentration of IND in the uterine tissue was doubled in the pregnant mice receiving LIP-IND-ORA compared to those that received IND alone, (LIP-IND-ORA: 1862.7±503.3 ng/g vs. IND: 965.1±311.7 ng/g, p=0.006) as shown in FIG. 7D. Moreover, there was a 2-fold reduction in levels of IND within the fetus of animals that were given LIP-IND-ORA as compared to those that received IND alone, (LIP-IND-ORA: 121.3±16.8 ng/g vs. IND: 245.3±61.7 ng/g, p=0.002). Overall, the uterine to fetus IND concentration ratio was four fold higher for LIP-IND-ORA vs. IND. These findings demonstrated the targeting of the LIP-IND-ORA to the pregnant uterus tissue associated with reduction in the placental passage of IND.

Figure 8A:
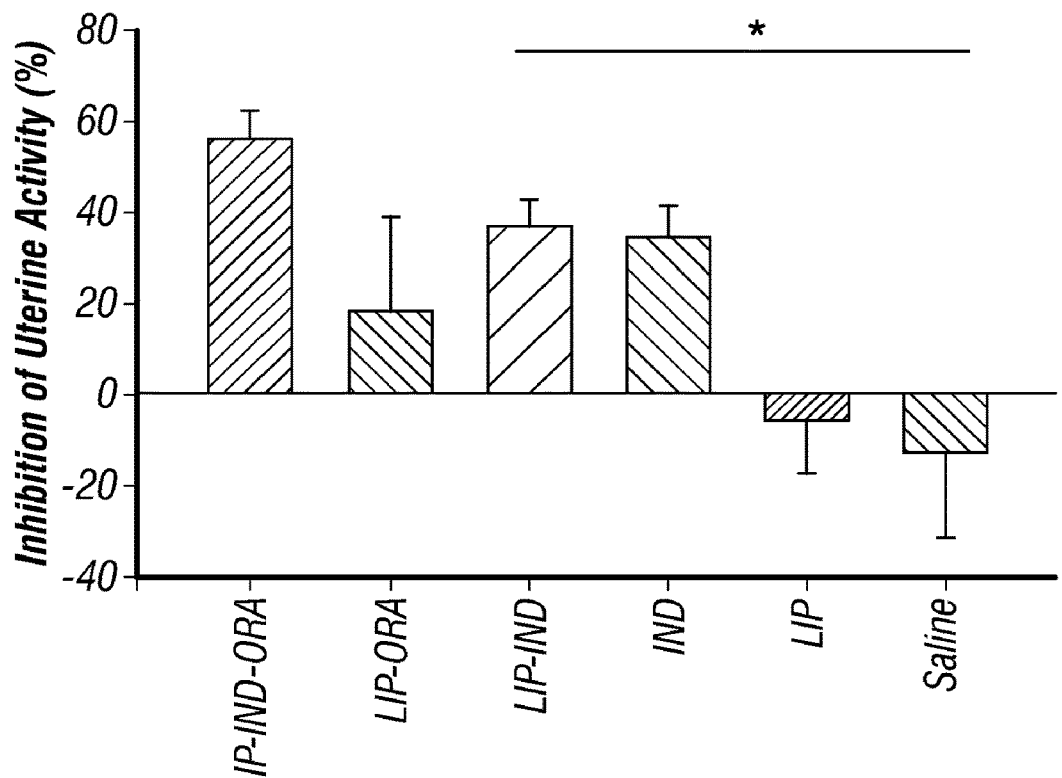
FIGS. 8A-8D: Inhibition of uterine contractility ex vivo. The efficacy of LIP-IND-ORA to inhibit contractility of uterus isolated from pregnant mice was demonstrated. (A) inhibition (%) of uterine contractions between LIP-IND-ORA, as compared to LIP-ORA, LIP-IND, IND, LIP and untreated control (saline, SAL) were determined in the absence of oxytocin (B) oxytocin induced uterine contraction (%) in the presence of various doses of oxytocin (an inducer of the uterine contractility). (C) Prostaglandin E2 ($PGE_2$) concentrations as determined by ELISA. (D) Representative myographs from ex vivo contractility experiments. Mean±SEM. n=6. *p-value<0.05, **p-value<0.01 vs. untreated control.
Figure 8B:
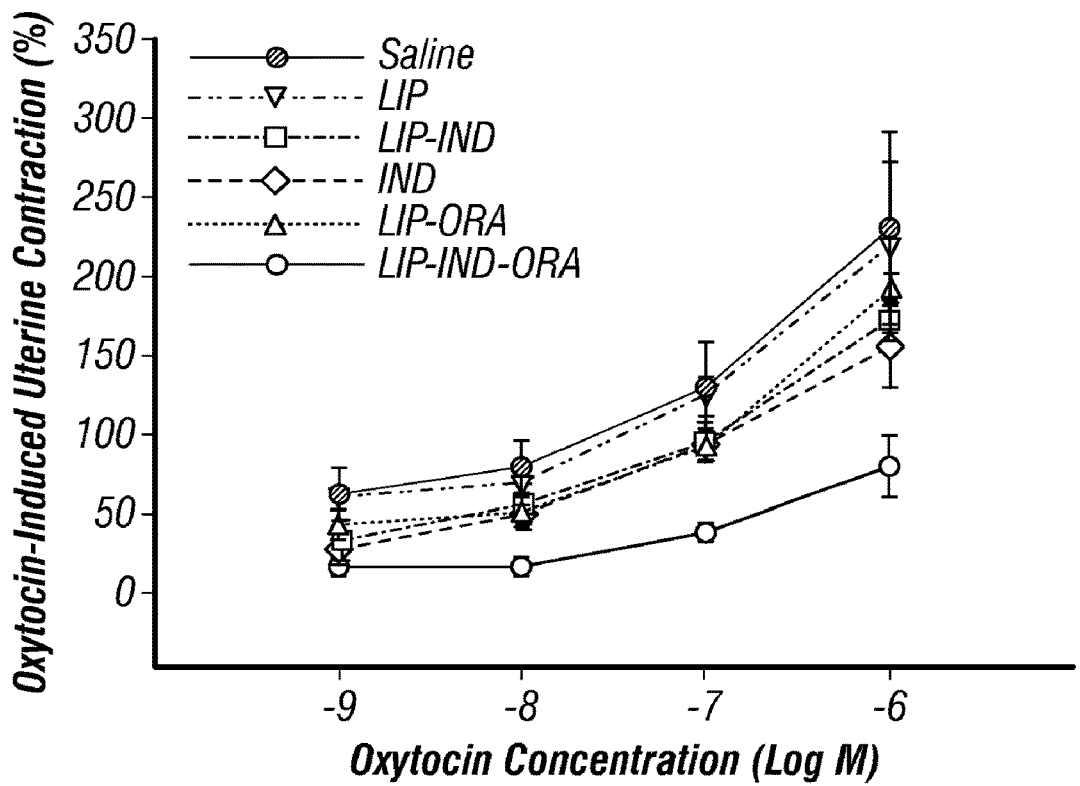
Figure 8C:
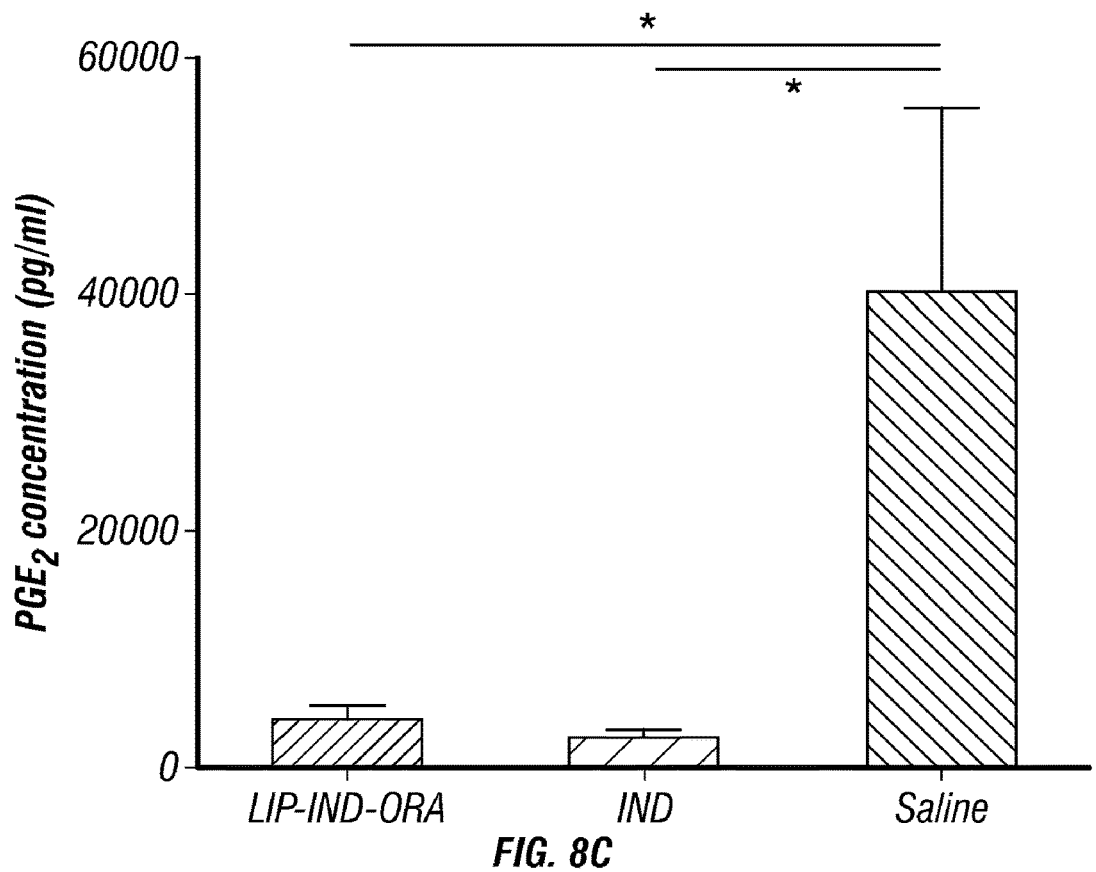
Figure 8D:
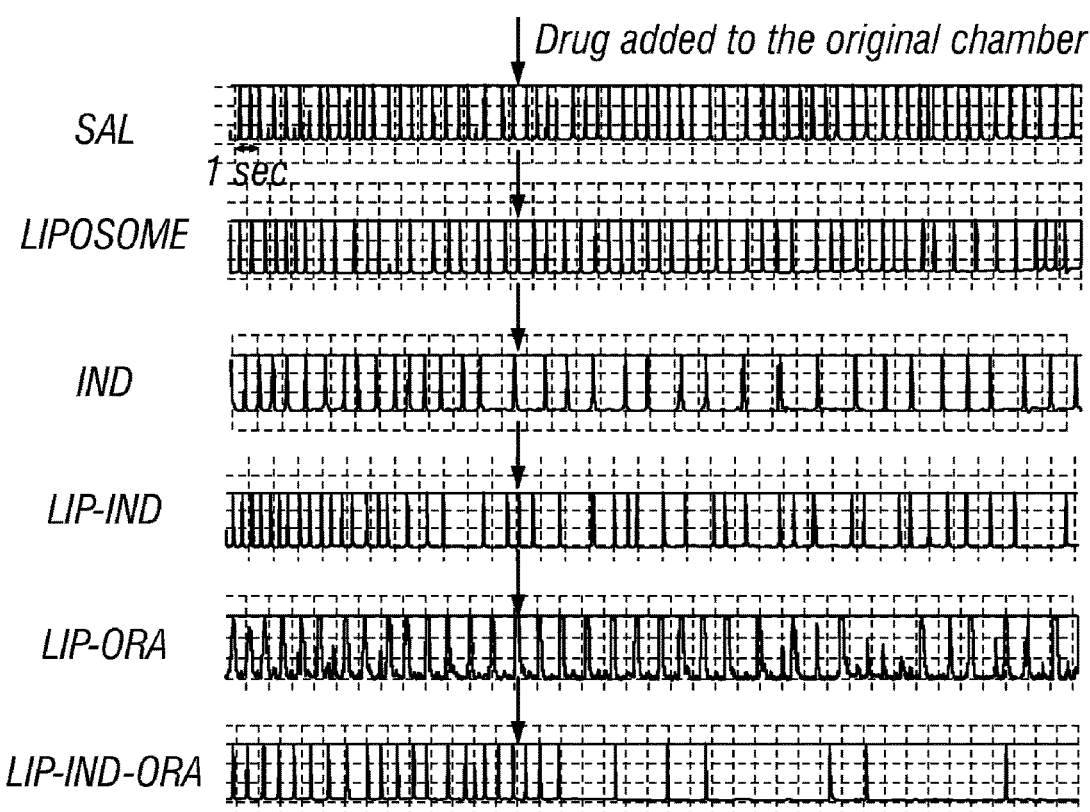

Uterine contractility ex vivo. The efficacy of the LIP-IND-ORA system in inhibiting the pregnant uterine contractility was examined ex vivo. LIP-IND-ORA significantly increased the percent inhibition of uterine contractions compared to treatment control (saline, SAL), (LIP-IND-ORA: 56.0±6.4% vs. SAL: −12.8±18.4%, p=0.003) [n=6 per group, mean±SEM] as shown in FIG. 8A. Moreover, LIP-IND-ORA significantly increased the percent inhibition of uterine contractions compared to LIP, (LIP-IND-ORA, 56.0±6.4, versus LIP −6.0±11.8 p=0.001). Interestingly, LIP-IND inhibited uterine contractions similarly to IND alone (36.8±5.9% vs. 34.3±6.6%, respectively), demonstrating the tocolytic efficacy of the drug while encapsulated in LIP. Finally, LIP-ORA showed no significant difference in uterine contractility (18.2±20.4) compared to all the other groups. Representation of the myograph experiments for each drug and its effect on uterine contractility are given in FIG. 8D. Since saline functioned as the control for the absence of a tocolytic agent, its exposure resulted in an increase in uterine contractions as designated by its negative value. The inhibition of uterine activity appeared to be more efficient with LIP-IND-ORA as compared to IND alone (IND: 34.3±5.9). Further, to mimic the oxytocin-induced contractions in the uterus, a dose response curve to oxytocin (OXY) was also performed. In this setting LIP-IND-ORA showed a decreased OXY induced contraction curve compared to both IND and SAL at all doses of oxytocin (FIG. 8B).

Figure 10:
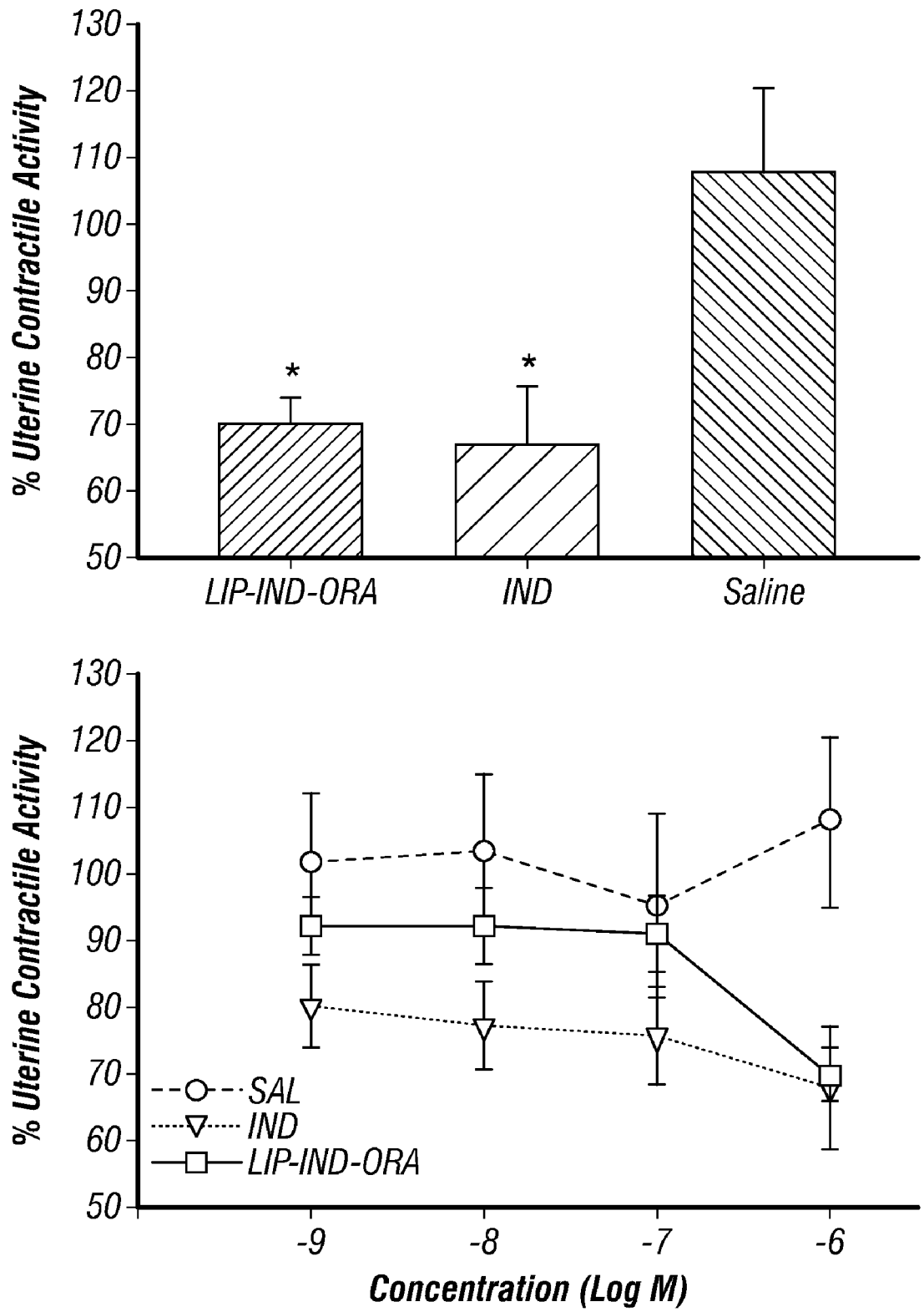
FIG. 10: Ex vivo human myometrial contractility studies. In an organ bath chamber, LIP-IND-ORA-A shows equivalent or superior activity in inhibiting uterine contractility in human uterine tissue models and suppresses oxytocin-inducted uterine contractions in mice compared to all other groups. *p<0.05.

In vitro human contractility studies: Strips from uterine biopsies obtained at cesarean section from non-laboring, term, healthy women were exposed to escalating doses ($10^{-9}$ to $10^{-6}$ mM) of IND and LIP-IND-ORA; saline was used as a control. At the highest concentration of $10^{-6}$, the percent uterine contractions was similar between IND and LIP-IND-ORA-A, and significantly reduced compared to SAL, (IND: 67.2±8.4% vs. LIP-IND-ORA: 69.9±8.4% vs. SAL: 107.2±12.6%, p<0.05) shown in FIG. 10.

To evaluate the pharmacological activity of IND encapsulated in the LIP-IND-ORA system, the levels of prostaglandin E2 (PGE2) were determined in the uterus. PGE2 levels were significantly reduced in the uterus exposed to LIP-IND-ORA and IND compared to SAL, (4,127.9±1, 178.6, 2,587.4±676.5 and 40,188.7±15,555.6 pg/mL, respectively, p=0.019) [n=6 per group, mean±SEM] as described in FIG. 8C. This illustrates that the encapsulation of IND within the targeted LIP, LIP-IND-ORA, does not alter the pharmacological activity of IND.

Figure 9:
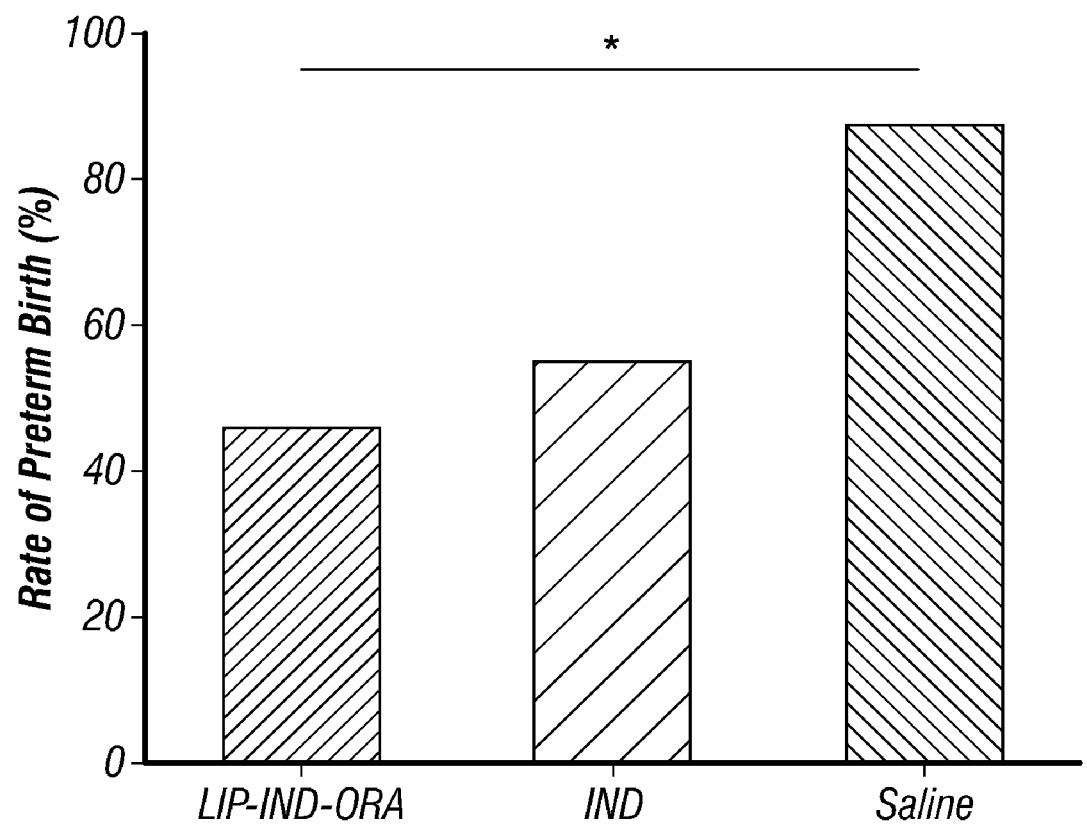
FIG. 9: In vivo therapeutic efficacy in prevention of preterm birth. The efficacy of LIP-IND-ORA to prevent preterm birth was tested in an LPS-induced preterm pregnant mouse model. Preterm birth rates were compared between LIP-IND-ORA (n=13), indomethacin (IND, n=11) and saline (n=8). *p-value=0.029 compared to saline control.

Preterm birth in vivo. LIP-IND-ORA significantly reduced the rate of LPS-induced preterm birth compared to SAL, (LIP-IND-ORA: 46.2% vs. SAL: 87.5%, p=0.029) as shown in FIG. 9. Although the rate of preterm birth decreased by 15% with LIP-IND-ORA compared to IND alone (IND: 54.5%), this was not statistically significant. Additionally, although the length of pregnancy in hours was prolonged by 31% in mice treated with LIP-IND-ORA compared to IND and SAL; this was not statistically significant, (LIP-IND-ORA: 44.0±4.5 h vs. IND: 30.0±4.9 h vs. SAL: 17.5±3.2 h, p=0.076).

Thus, the successful delivery of indomethacin directly to the pregnant uterus was demonstrated with the customized liposomes consistently across three approaches, in vitro, in vivo and ex vivo. Additionally, there was significant enhancement of indomethacin's tocolytic efficacy, while reduction in the drug levels detected in the fetus. The targeted liposome significantly decreased prostaglandin levels in the uterus thereby inhibiting uterine contractions. This resulted in prolonging pregnancy by 31% and reducing the rate of preterm birth by 15% as compared to the free drug. To enable faster clinical translation of the proposed approach, a clinically used[33] oxytocin receptor antagonist (ORA, or atosiban) was used as the targeting element. At therapeutic concentrations, ORA was shown to induce minimal adverse effects. In the current study, the total administered dose of ORA was several times lower than the minimal therapeutic dose and, consequently, ORA levels were not detectable in the maternal organs by LC-MS/MS. Thus, the goal of using ORA as a safe targeting moiety for pregnant women was successfully in delivering indomethacin to the uterus directly. The principles of nanomedicine have been applied to optimize tocolytics for the treatment of preterm labor, and the novel drug delivery system can provide a path for a new paradigm-shifting direction to advance the field of obstetrics.

Example 3

Materials and Methods

Liposome design and fabrication. LIP, LIP-IND, LIP-ORA and LIP-IND-ORA were prepared by lipid hydration-extrusion method. First, the lipids were dissolved in 3 mL ethanol at the following concentrations: 9.6-12.2 mg soy bean phosphatidylcholine (Lipoid 5100, Lipoid, Germany), 0-0.77 mg cholesterol (Sigma) and 1-3 mg DSPE-PEG (2000) Carboxylic Acid (1,2-distearoyl-sn-glycero-3-phosphoethanolamine-N-[carboxy(polyethylene glycol)-2000] (ammonium salt)) (Avanti, Alabama, USA). To fluorescently label LIP, fluorescent phospholipid Lissamine rhodamine B 1,2-dihexadecanoyl-sn-glycero-3-phosphoethanolamine, triethylammonium salt (rhodamine-DHPE, Invitrogen), 2% of the total lipid was incorporated to all liposome formulations. 0.45 mg of IND (Sigma) was added to the above ethanolic mixture for LIP-IND and LIP-IND-ORA formulations. A thin film was formed by evaporating the solvent for 30 minutes (min), 41° C. at 150 rpm using rotary evaporator (Rotavapor, Buchi, Switzerland). The film was rehydrated with 1 mL PBS pH 7.2. Liposomes were extruded 10 times using each of the following 800-, 400-, and 200-nm Nuclepore Track-Etch Membrane (Whatman) filters with Lipex Biomembrane extruder. The resulting liposomes were ultracentrifuged (60,000 xg, 2 hours [h]) using Solvall WX ultra series ultracentrifuge (Thermo Scientific). Supernatant was removed and the LIP and LIP-IND were resuspended with 1 mL PBS.

ORA-NHS was prepared for conjugation with liposome by adding 1.9 mg EDC (1-ethyl-3-[3-dimethylaminopropyl] carbodiimide) (Life technologies) and 2.9 mg NHS (N-hydroxysuccinimide) to each mg ORA in MES buffer and incubated in rotator at room temperature (RT) for at least 15 min. For LIP-ORA and LIP-IND-ORA preparation, the systems were resuspended with 1 mL MES (2-[morpholino] ethanesulfonic acid) buffer containing ORA-NHS equivalent to 0.35 mg ORA weight. Conjugation was conducted at RT overnight, and unbound ORA were washed from liposome by ultracentrifugation (60,000 xg, 2 h).

The size and zeta potential of the liposomes were assessed by dynamic light scattering using Zetasizer (Malvern, Worcestershire, UK). Five separately prepared batches of each formulation were analyzed in triplicates each. The morphology and structure of LIP were observed by scanning electron microscopy as previously described (Refuerzo et al., 2015).

The levels of IND in the LIP were assessed using high-performance liquid chromatography (HPLC). Supernatant from ultracentrifugation after conjugation was used for measurement of unbound ORA concentration to determine the ORA conjugation efficiency indirectly. An aliquot of LIP-ORA and LIP-IND-ORA were dissolved in ethanol and used for direct measurement of conjugated ORA.

HPLC method for indomethacin detection in the formulation: IND was analyzed by isocratic detection using UV diode-array HPLC system Column Hitachi Elite LaChrom, Column oven L-2300, Autosampler L-2200, Diode Array Detector L-2455, Pump L-2130 Hitachi D-2000 Elite v3.0 software. Kinetex 2.6µ XB-C18 100 Å A (100×4.6 mm, Phenomenex) column was used for the separation at 237 nm. Chromatography was performed using an isocratic elution with mobile phase composed of 0.2% phosphoric acid in acetonitrile at a flow rate of 0.6 ml/min with average retention time of 7.2 min.

Figure 11A:
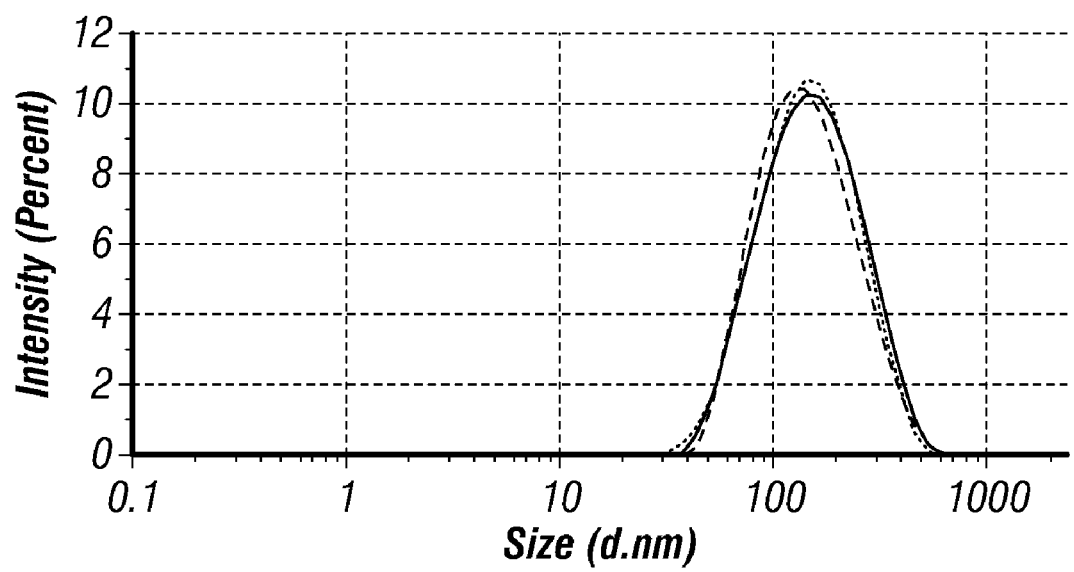
FIGS. 11A-11B: Characterization of LIP-IND-ORA formulated using NanoAssembler. The targeted LIP are very uniform in size and have narrow size distribution (A) and zeta potential (B). NanoAssembler also allows the production of reproducible larger quantities of LIP.
Figure 11B:
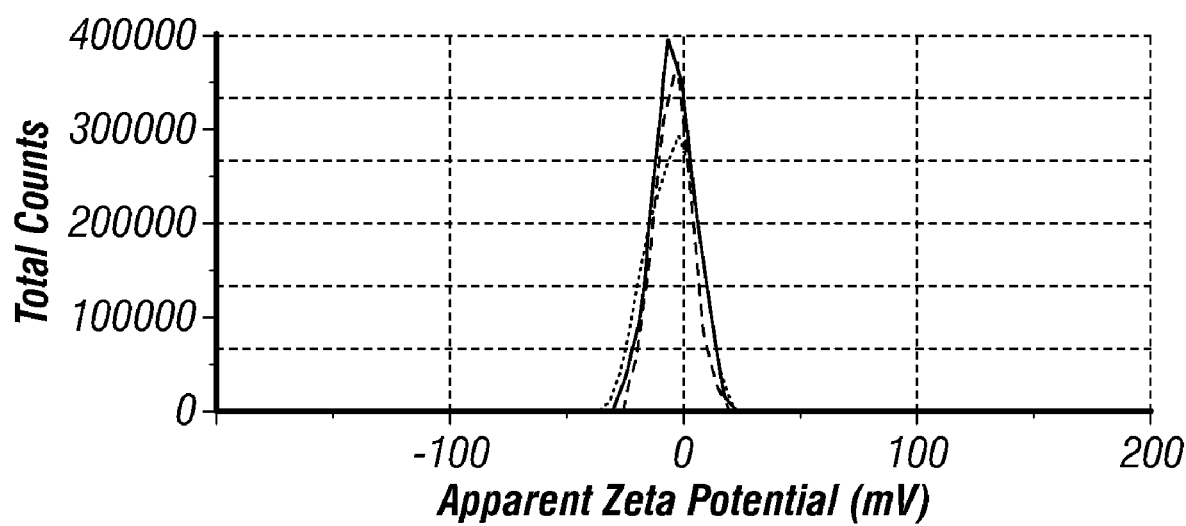

LIP-IND-ORA were prepared using a microfluidics device, NanoAssembler™ (Precision NanoSystems, Inc) (Ramishetti et al., 2015) that has been proven to be able to improve liposome production improve reproducibility and scalability (Belliveau et al., 2012; Zhigaltsev et al., 2012; Kastner et al., 2014), and in accordance to GLP as well as GMP practice. In brief, liposomes are prepared by mixing one volume of solvent containing 30 µM S100 soybean phosphatidylcholine (Lipoid, Ludwigshafen, Germany), 6 µM cholesterol (Sigma, St. Louis, Mo.), 3.8 µM Indomethacin (Sigma, St. Louis, Mo.), and 1.1 µM DSPE-PEG(2000) Carboxylic Acid (Avanti Polar Lipids, Alabaster, Ala.) and two volumes of distilled water using dual syringe pump (model S200, kD Scientific, Holliston, Mass.) to drive the solutions through the micro mixer at a combined flow rate of 9 mL/min. The produced liposomes were dialyzed against phosphate buffered saline (PBS) (pH 7.4) for 16 h to remove ethanol. The resulting liposomes had hydrodynamic diameter of ~167 nm, Pdl of 0.14 and ζ-potential of −5.36 mV as measured by dynamic light scattering (Malvern Zetasizer, Malvern Instruments, Malvern, UK). The conjugation of liposome with ORA/Atosiban was conducted following the liposome production using 3 µM EDC (1-ethyl-3-[3-dimethylaminopropyl]carbodiimide) (Life technologies, Carlsbad, Calif.) and 8.3 µM NHS (N-hydroxysuccinimide) (Life technologies, Carlsbad, Calif.) in MES buffer (PolyLink Protein Coupling Kit, Polysciences, Warrington, Pa.) as catalyst. 0.3 µM ORA was dissolved in the catalyst mixture and liposomes were added to the solution and let to react in rotator at room temperature (RT) for at least 15 min. Conjugation efficiency was determined to be 51.8%. The addition of ORA to LIP-IND did not alter the drug encapsulation and fluorescent properties of the nanoparticles (FIGS. 11A-11B).

Animals: Pregnant female (strain CD1, stock N 022) mice were purchased form Charles River. For the targeting efficiency and the biodistribution studies, mice were used at term gestation, gestation day 18 (GD 18). For the ex vitro uterine contractility study pregnant mice were used at gestational day 19 (GD 19), just before mice are about to deliver and uterine contractility is maximal. For the preterm study, mice were obtained at mid gestation (GD 14). The mice were housed separately in temperature and humidity-controlled quarters with constant 12:12-hours light-dark cycles.

In addition, human biopsies were obtained from two women undergoing cesarean section to create a cell culture of uterine cells. Both were obtained from singleton, non-laboring pregnancies at 39 weeks of gestation (Human A is Hispanic, BMI 29 kg/m² and Human B is Caucasian, BMI 33 kg/m²).

Targeting efficiency in vitro. To confirm the localization of the oxytocin receptor on uterine cells, a pregnant mouse uterine cell line was created from two timed-pregnant CD1 pregnant mice (Charles River) on gestational day (GD) 19. Mice were individually housed in an environmentally controlled vivarium under 12 h light and dark cycles. Animals were fed ad lib throughout the experiment. After CO2 inhalation euthanasia, laparotomy was performed and the pregnant uterus was retrieved and placed in Hank's balanced salt solution. The uterine tissue was cut into 1-2 mm fragments with a razor then digested in 0.1% trypsin (Sigma, USA) and 0.1% deoxyribonuclease (Sigma, USA) for 30 min at 37° C. in shaker incubator, followed by 0.1% collagenase (Sigma, USA) for another 30 min. After filtering the tissue through gauze, the cells were washed then plated on collagen I-coated 75 mm flasks (BD Biosciences, USA) with RPMI 1640 media (Sigma, USA), 10% fetal bovine serum (FBS, Sigma, USA) and Pen-Strep (Sigma, USA). The media was changed daily until Day 4.

The study of liposome attachment was conducted in triplicates, where the cells were seeded with a density of $2\times10^5$ cells/mL and 0.5 mL/well in 8-well chamber slide. The cells were incubated at 37° C. overnight for cell attachment. 10 µL of either targeted or non-targeted liposomes that were tagged with lissamine rhodamine were added to each well and gently shaken for a homogenous distribution in the well. The slides were incubated at 37° C. for 4 h to allow for interaction between cells and liposomes. After the incubation, the medium containing liposomes were discarded and the cells were washed twice with PBS. Cells were fixed afterwards with 4% paraformaldehyde in PBS for 30 min. Slide chambers were removed with the provided slide separator and the slides were mounted using Prolong Gold Antifade reagent (Life Technologies) and sealed with Cytoseal XYL (Thermo Scientific). Fluorescence signal from liposomes was detected using Nikon Eclipse Ti fluorescence microscope and analyzed using NIS Elements software.

For flow cytometry analysis, the cells were detached from the flasks by using the cell dissociation buffer (Life Technologies). Medium was removed from the flask and the cell layer was washed with calcium-/magnesium-free PBS. After PBS removal, 2 mL of the cell dissociation buffer was added to the cells and the flask was incubated at 37° C. for 10 min. Cells that are still attached after the time were detached by firmly tapping the flask. The cells were gathered by addition of medium and counted. At least $2\times10^5$ cells were incubated with targeted and non-targeted liposomes for 4 h at 37° C. After incubation time, the medium containing liposomes were removed by centrifugation at 400×g for 5 min. The cells were analyzed using BD FACS Fortessa (Becton Dickinson, San Jose, CA) detected in the PerCP channel, using untreated cells as control. The data was post-processed using FCS Express Flow 5 software.

Biodistribution study in vivo. The concentration of IND delivered to the pregnant uterus from LIP-IND-ORA was compared to free IND using an established in vivo pregnant mouse model. On GD 18, timed-pregnant CD1 mice (N=6/group) were randomly allocated to receive either LIP-IND-ORA, IND or saline (SAL) via tail vein injection at a volume of 0.1 mL. When the drug was used (LIP-IND-ORA or IND), the dose of IND was 1 mg/kg (range 50-60 mg per animal based on maternal weight). The in vivo doses were maintained across the study. After 4 h, pregnant mice were sacrificed by CO2 inhalation, followed by laparotomy to retrieve maternal liver, uteri, placentas and fetuses. The onset of action of LIP-IND-ORA is unknown when administered intravenously. However, indomethacin's onset of action is 2-3 h when given orally to humans and rodents, and is 4-5 h when encapsulated with liposomes and administered via intraperitoneal injection. Preliminary investigations showed an increase of IND in the uterus and reduction in the fetus when encapsulated within LIP after 4 h following administration39. Based on these prior studies, 4 h was chosen as the period of exposure.

Liposome distribution was determined by immunofluorescence as previously described (Refuerzo, et al., 2015). Briefly, tissue localization of LIP was qualitatively assessed using fluorescent microscopy identifying the absence or presence of LIP (tagged with fluorescent dye as previously described) within the liver, uterus, placenta and fetus. For this analysis, the excised tissues were placed in cryo-molds, embedded in the cryo-preserving media (OCT) and immediately frozen using liquid nitrogen. The blocks were stored in −80° C. until sectioning using cryo-microtome. During mounting on the slides, the tissue slices were stained with DAPI (4',6-diamidino-2-phenylindole) fluorescent stain to identify nuclear structures of cells. Images were taken with the BX51 fluorescent microscope (Nikon, USA) using filters for DAPI and Cy3 at 100×magnification. Six animals per group were utilized in this study and their organs were sectioned and analyzed. Quantification was conducted in randomly selected area of at least 9 areas per animal to ensure the objectivity, while an image was chosen to represent the fluorescence signal. Quantitative biodistribution of liposome was determined using an NIS elements image processing software (Nikon, USA). The binary area of a fluorescent signal reported in prn2 as mean±sem.

The concentrations of indomethacin in IND and LIP-IND-ORA samples were determined by LC-MS/MS using multiple reactions monitoring assay with Phenacetin-ethoxy-D5 (Sigma, USA) as internal standard. Uterine and fetal tissues were homogenized in 1 mL of ice-cold methanol/water (7:3 v/v). Phenacetin (final concentration 20 ng/mL) was added to each sample before centrifugation at 15,000 rpm for 10 min. Supernatant was dried under nitrogen and reconstituted in 0.1% formic acid aqueous solution followed by protein precipitation with acetonitrile (1:2). Samples were centrifuged again, supernatant was transferred to vial and 10 µL was injected to Shimadzu triple quad 8040 MS connected to LC system. Indomethacin concentrations were determined in ng/mL against calibrators. Calibration curve was prepared by spiking in calibrator levels (15.6; 31.2; 62.4; 125; 250 and 500 ng/mL) in control tissue (no indomethacin) followed by extraction procedure identical to sample preparation. Method parameters were: LOD=3.9 ng/mL (accuracy 76%, S/N>3); LOQ=15.6 ng/mL (accuracy 85%; CV<10%; S/N>10) with correlation coefficient for linear regression $R^2$=0.992. Indomethacin concentrations were further normalized per tissue weight (ng/g) and reported as mean±SEM.

Uterine contractility ex vivo. An established ex vivo pregnant mouse or human models of uterine contractility was used to measure the ability of LIP-IND-ORA to inhibit uterine contractions. For mice, on GD19, timed-pregnant animals (N=6) underwent CO2 inhalation euthanasia, the maternal uteri were excised and placed into Krebs physiological solution. In the case of human tissue, strips from uterine biopsies obtained at cesarean section from non-laboring, term, healthy women were used. Uterine ring segments, 4 mm in width, were cut, and the fetuses and placentas were gently removed. The uterine rings were positioned between tungsten-wire (250 µm in diameter) stirrups and placed in an organ chamber containing 10 mL Krebs buffer, bubbled with 5% carbon dioxide in 95% oxygen maintained at constant temperature and pH (37° C., pH 7.4). Passive tension was gradually applied to the optimal level of 1 g during an equilibration period of 60 min. Once the uterine tissue contracted spontaneously, uterine rings were then incubated with either: LIP-IND-ORA (10-5 mol/L), LIP-ORA, LIP-IND (10-5 mol/L), IND (10-5 mol/L), LIP and saline (SAL) as control for 40 min. After incubation of the study drugs, dose response curves to oxytocin (OXY) were obtained (10-9 mol/L to 10-6 mol/L; 20 min between OXY doses) to produce increased stable uterine contractions. The final concentration of IND administered into the organ chamber is equal to the concentration of IND (1 mg/kg) in LIP-IND and LIP-IND-ORA. To confirm tissue viability, potassium chloride (KCL 60 mmol/L) was added in each chamber at the end of the experiment. OXY and IND (Sigma, USA) were dissolved in water and ethanol respectively. The final concentration of ethanol in the organ chamber solution (1.3×10-4 mol/L) was 130 times inferior to a plasma concentration that could possibly account for a tocolytic effect.

Changes in isometric tension were recorded with isometric force transducers (Harvard Apparatus, South Natik, Mass.) connected and stored to an online computer with data acquisition software (WINDAQ-200; DATAQ). The data was acquired and analyzed using Windaq data acquisition system (Dataq Instruments Inc, Akron, Ohio). Spontaneous contractile activity for each uterine ring was analyzed as an integral activity over 40 min before (basal activity) and after application of each study drug. Baseline activity was defined as the integral activity over the 40 min following stabilization of uterine contractions. The effect of the IND alone and LIP-IND-ORA were determined by calculating the integral activity expressed as a percent change from the baseline integral activity. OXY induced contractile response was expressed as an integral activity over 20 min of each OXY dose and the baseline uterine contractility54,55,56. The percent inhibition of uterine contractions and the dose response curve to oxytocin were calculated using software (Sigma Plot and GraphPad Prism, version 3.00 for Windows; GraphPad Software, San Diego, Calif.). Data was expressed as mean±SEM.

Since the pharmacological action of IND involves the inhibition of prostaglandin production by cyclooxygenase, prostaglandin E2 (PGE2) levels were measured in uterine tissue using ELISA (ADI-901-001, Enzo Life Science, New York, USA). Another set of pregnant CD1 mice at GD 19 (n=5) was used to evaluate uterus PGE2 levels. The uterus from the pregnant mice was obtained as described previously and incubated with LIP-IND-ORA, IND or saline as control for 40 min. The 40 min exposure time was chosen since this was the same length of time the uterine tissue was exposed to LIP-IND-ORA or IND in the uterine contractility experiments. PGE2 levels in each sample were then determined based on the instructions in the ELISA kit (ADI-901-001, Enzo Life Science, New York, USA). The concentration of PGE2 were expressed as pg/mL and reported as the mean±SEM.

Preterm birth in vivo. The established in vivo preterm pregnant mouse model was used to test the ability of LIP-IND-ORA to prevent preterm birth. LPS is a commonly used model to induce labor in murine models. On GD 16, timed-pregnant CD1 mice were administered lipopolysaccharide (LPS, Sigma, USA) (25 µg/kg) via intraperitoneal injection. Animals were randomly divided into 3 groups and given daily treatments via tail vein injection according to group randomization: IND (N=11), LIP-IND-ORA (N=13), and SAL (N=8). IND concentrations were again 1 mg/kg based on prior studies. Since the LIP-IND-ORA solution color was visibly pink and due to limited resources to create a placebo, the randomization was not blinded. Each day after the LPS administration, the preterm birth rate was determined as the number of pregnant mice spontaneously delivering prior to GD18. Animals were housed in single cages and were monitored by either direct observation or by video camera for the duration of the treatment period to confirm timing of delivery. The rate of preterm birth was expressed as percent and length of pregnancy after LPS administration was expressed in hours. Results were reported as median±sem.

A sample size calculation was performed based on prior experiments involving IND in the prevention of preterm birth in pregnant rodents. Mice treated with IND had a 30% rate of preterm birth compared to 90% in control. Based on an effect of 33% with an α of 0.05 (2-tailed) and 1β of 0.80, we determined that 7 maternal mice were needed in each group.

Statistical Analysis. Differences in isometric tensions of myometrium, IND concentrations in the uterus and fetus, $PGE_2$ concentrations in the uterus, preterm birth rates and length of pregnancy between groups were analyzed using one-way analysis of variance with Tukey post hoc test. STATA software (version 12.1) were used and a P value<0.05 was considered significant.

Calculation of ORA concentration in LIP-IND-ORA as compared to the human dose. The dose of ORA was 35.8 µg/mouse (~50 g) or approximately 7 mg/kg, which is, based on the accepted NIH conversion factors (ACUC guidance based on (Freireich, et al., 1966)), equivalent to a human dose of 0.58 mg/kg.

In humans, ORA (Atosiban®) is delivered as an infusion in three steps: Initial loading dose of 6.75 mg, followed by 300 µg/min for 3 hours (54 mg) and up to 45 hours subsequent intravenous infusion at 100 µg/min. So the overall dose is in the range of 70-330 mg/person or (considering the average weight of 60 kg) 1.2-5.5 mg/kg. Thus, the given dose of ORA is below the physiologically relevant concentrations of the drug.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,162,282
U.S. Pat. No. 4,310,505
U.S. Pat. No. 4,533,254
U.S. Pat. No. 4,728,575
U.S. Pat. No. 4,728,578
U.S. Pat. No. 4,737,323
U.S. Pat. No. 4,921,706
U.S. Pat. No. 5,030,453
U.S. Pat. No. 5,855,911
U.S. Pat. No. 5,962,016
U.S. Pat. No. 6,680,068
U.S. Patent App. 2004/0208921
WO02/100435A1
WO03/015757A1
WO04/002453A1
WO04029213A2
U.K. Patent Application GB 2193095 A
International Application PCT/US85/01161
International Application PCT/US89/05040
Balley et al., 2012.
Bangham et al., 1965.
Belliveau et al., 2012.
Cheng et al., 1987.
Deamer and Uster, 1983.
Farhood et al., 1995.
Flenady et al., Oxytocin receptor antagonists for inhibiting preterm labour. The Cochrane database of systematic reviews; 6:CD004452, 2014.
Freireich, E J, et al. Quantitative comparison of toxicity of anticancer agents in mouse, rat, dog, monkey and man. *Cancer Chemother Rep.;* 50(4):219-244, 1966.
Garland M. Pharmacology of drug transfer across the placenta/. Obstet gynecol Clin North Am; 25:21-42, 1998.
Ghosh and Bachhawat, 1991.
Gregoriadis, 1979.
Hope et al., 1985.
Kastner et al., 2014.
Liposome Technology, 1984.
Major et al., Tocolysis with indomethacin increases the incidence of necrotizing enterocolitis in the low-birth-weight neonate. Am J Obstet Gynecol; 170(1 Pt 1):102-106, January 1994.
Mayer et al., 1986.
Mayhew et al. 1987.
Mayhew et al., 1984
Ramishetti et al., 2015.
Refuerzo et al., Liposomes: a nanoscale drug carrying system to prevent indomethacin passage to the fetus in a pregnant mouse model. Am J Obstet Gynecol.; 212(4):508 e501-507, April 2015.
Suarez et al., Indomethacin tocolysis and intraventricular hemorrhage. Obstet Gynecol; 97(6):921-925, June 2001.
Syme et al., Drug transfer and metabolism by the human placenta. Clin Pharmacokinet; 43(8):487-514, 2004.
Szoka and Papahadjopoulos, 1978.
van der Aa et al., Mechanisms of drug transfer across the human placenta. Pharmacy world & science: PWS.;20(4): 139-148, August 1998.
Zhigaltsev et al., 2012.

What is claimed is:

1. A pharmaceutical composition comprising a tocolytic agent encapsulated in a liposome, wherein the liposome comprises a targeting moiety that binds to an oxytocin receptor, wherein the targeting moiety is an oxytocin receptor antagonist selected from the group consisting of atosiban, retosiban, barusiban or epelsiban and wherein the targeting moiety is conjugated to the surface of the liposome.

2. The pharmaceutical composition of claim 1, wherein the tocolytic agent is an agent that crosses the placenta.

3. The pharmaceutical composition of claim 1, wherein the tocolytic agent comprises β2-adrenergic agonist, a calcium-channel blocker, a oxytocin receptor antagonist (ORA), prostaglandin F2α receptor inhibitor, a nitric oxide donor or a nonsteroidal anti-inflammatory drug (NSAID).

4. The pharmaceutical composition of claim 3, wherein the β2-adrenergic agonist comprises terbutaline, ritodrine, bedoradrine sulfate, MN-221, isoxsuprine, hexoprenaline, nylidrine, salbutamol or fenoterol.

5. The pharmaceutical composition of claim 3, wherein the calcium-channel blocker comprises nifedipine or nicardipine.

6. The pharmaceutical composition of claim 3, wherein the ORA comprises carbetocin, TC OT 39, WAY 267464 dihydrochloride, [Thr4]OT, [HO1][Thr4]OT, [Thr4,Gly7] OT and [HO1][Thr4,Gly7]OT.

7. The pharmaceutical composition of claim 3, wherein the prostaglandin F2α receptor inhibitor comprises OBE-001, OBE-002 or PDC-31.

8. The pharmaceutical composition of claim 3, wherein the NSAID comprises indomethacin, sulindac, ketorolac, celecoxib, rofecoxib or nimesulide.

9. The pharmaceutical composition of claim 8, wherein the composition comprises indomethacin.

10. The pharmaceutical composition of claim 3, wherein the Nitric oxide donor comprises sildenafil, nitric oxide or nitroglycerin.

11. The pharmaceutical composition of claim 1, wherein the targeting moiety is conjugated to a PEGylated phospholipid.

12. The pharmaceutical composition of claim 11, wherein the PEGylated phospholipid comprises 1,2-Distearoyl-sn-glycero-3-phosphoethanolamine (DSPE).

13. The pharmaceutical composition of claim 12, wherein the PEGylated phospholipid comprises DSPE-PEG(2000) carboxylic acid.

14. The pharmaceutical composition of claim 13, wherein the targeting moiety comprises DSPE-PEG(2000)-atosiban.

15. A method of treating a pregnant patient to slow or prevent preterm labor comprising administering to the patient an effective amount of the pharmaceutical composition of claim 1.

* * * * *